United States Patent
Matonick

(10) Patent No.: US 11,497,669 B2
(45) Date of Patent: Nov. 15, 2022

(54) SYSTEMS, DEVICES, AND METHODS FOR TESTING SUTURE PERFORMANCE UNDER STATIC AND DYNAMIC CONDITIONS

(71) Applicant: Ethicon, Inc., Somerville, NJ (US)

(72) Inventor: John Matonick, Warren, NJ (US)

(73) Assignee: Ethicon, Inc., Raritan, NJ (US)

(*) Notice: Subject to any disclaimer, the term of this patent is extended or adjusted under 35 U.S.C. 154(b) by 872 days.

(21) Appl. No.: 16/396,653

(22) Filed: Apr. 27, 2019

(65) Prior Publication Data
US 2020/0337924 A1 Oct. 29, 2020

(51) Int. Cl.
| | | |
|---|---|---|
| A61G 13/10 | (2006.01) | |
| A61B 17/04 | (2006.01) | |
| A61G 13/00 | (2006.01) | |
| A61M 5/168 | (2006.01) | |
| A61B 90/00 | (2016.01) | |
| A61G 13/12 | (2006.01) | |

(52) U.S. Cl.
CPC ....... A61G 13/101 (2013.01); A61G 13/0063 (2016.11); A61M 5/16854 (2013.01); A61B 17/0469 (2013.01); A61B 90/06 (2016.02); A61B 2090/0807 (2016.02); A61G 13/12 (2013.01)

(58) Field of Classification Search
CPC .......................... A61G 13/101; A61B 17/0469
See application file for complete search history.

(56) References Cited

U.S. PATENT DOCUMENTS

| | | | |
|---|---|---|---|
| 4,428,571 A | | 1/1984 | Sugarman |
| 4,538,595 A | * | 9/1985 | Hajianpour .......... A61H 1/0266 482/901 |
| 4,549,534 A | * | 10/1985 | Zagorski ............. A61H 1/0259 601/104 |
| 4,653,479 A | * | 3/1987 | Maurer .................... A61H 1/02 607/66 |
| 7,152,261 B2 | | 12/2006 | Jackson |

(Continued)

FOREIGN PATENT DOCUMENTS

EP 2753286 10/2015

OTHER PUBLICATIONS

S. Nade et al., "Pressure-Volume Relationships and Elastance in the Knee Joint of the Dog," J. Physiol, 1984, vol. 357, pp. 417-439.

(Continued)

*Primary Examiner* — Christian A Sevilla

(57) ABSTRACT

A system for testing sutures includes a test bench having a rotatable table, a framework supporting the test bench and the rotatable table above a surface, and a continuous passive motion (CPM) machine mounted on the rotatable table. The CPM machine is configured to rotate between a first position in which the CPM machine is upright and located above the rotatable table and a second position in which the CPM machine is inverted and located below the rotatable table. The system includes a fluid supply subsystem for directing an infusion fluid toward the CPM machine, a pump for circulating the infusion fluid in the fluid supply subsystem, a heat exchanger for heating the infusion fluid, a fluid (Continued)

collection tray located below the CPM machine and the rotatable table, and a pressure monitoring subsystem for monitoring a pressure level of the infusion fluid.

20 Claims, 26 Drawing Sheets

(56) References Cited

U.S. PATENT DOCUMENTS

| | | | |
|---|---|---|---|
| 7,343,635 B2 | 3/2008 | Jackson | |
| 8,888,718 B2 | 11/2014 | Siston et al. | |
| 8,978,180 B2 | 3/2015 | Jackson | |
| 2002/0173796 A1* | 11/2002 | Cragg | A61B 17/1757 606/86 R |
| 2003/0135137 A1* | 7/2003 | Splane, Jr. | A61G 13/009 601/24 |
| 2012/0124742 A1* | 5/2012 | Soto | A61G 13/121 5/600 |
| 2016/0120726 A1 | 5/2016 | Moriarty et al. | |
| 2017/0312158 A1 | 11/2017 | Blackwell | |

OTHER PUBLICATIONS

L. Wood et al., "Response of Slowly Adapting Articular Mechanoreceptors in the Cat Knee Joint to Alterations in Intra-Articular Volume," Annals of the Rheumatic Diseases, 1984, vol. 43, pp. 327-332.

K. Kharat, "Closure in Knee Replacement Surgery," Journal of Orthpaedic Case Reports, Jul.-Sep. 2012, pp. 31-32.

P. Kadimcherla et al., "Knee Arthrotomy Closure With Barbed Suture in Flexion Versus Extension: A Porcine Study," J. Arthroplasty, Nov. 2014, vol. 29, Issue 11, pp. 2211-2213.

S. Cerciello et al., "The Role of Wound Closure in Total Knee Arthroplasty: A Systemic Review on Knee Position," Knee Surg Sports Traumatol Arthrosc, Mar. 29, 2016, 7 pp.

J. Vakil et al., "Knee Arthrotomy Repair With a Continuous Barbed Suture," The Journal of Arthroplasty, 2011, vol. 26, No. 5, pp. 710-713.

M. Nett et al., "Water-Tight Knee Arthrotomy Closure: Comparison of a Novel Single Bidirectional Barbed Self-Retaining Running Suture Versus Conventional Interrupted Suture," The Journal of Knee Surgery, 2011, vol. 24, No. 1, pp. 55-59.

* cited by examiner

FIG. 32
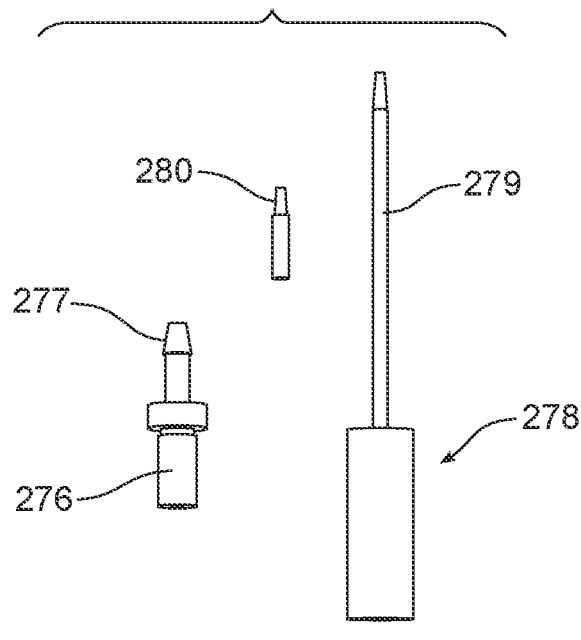
FIG. 33
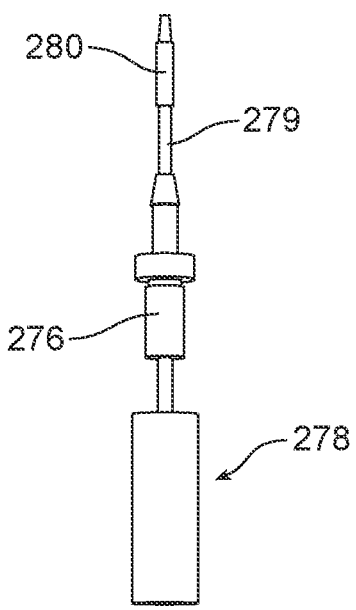
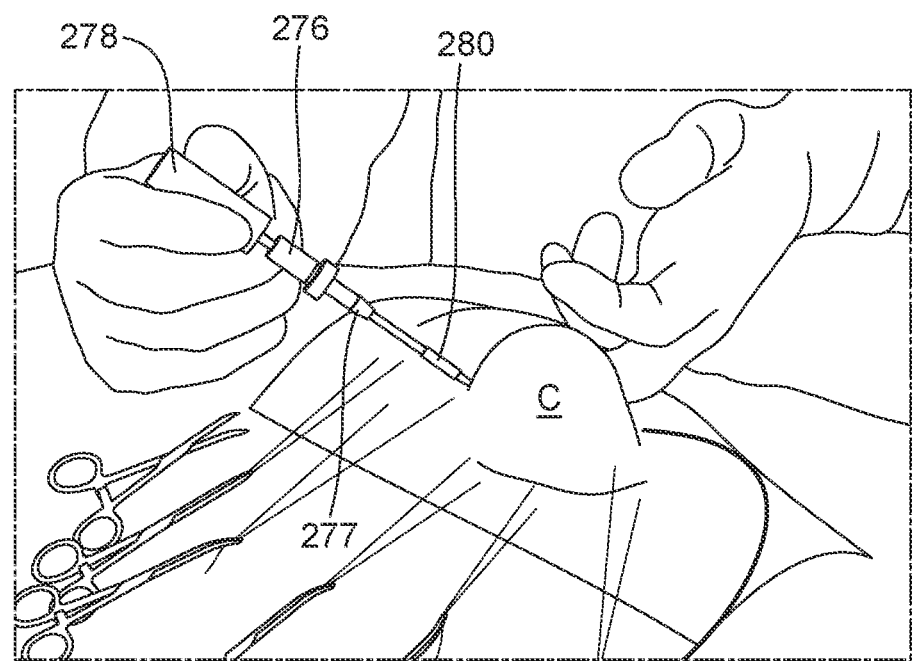
FIG. 34A

SYSTEMS, DEVICES, AND METHODS FOR TESTING SUTURE PERFORMANCE UNDER STATIC AND DYNAMIC CONDITIONS

BACKGROUND OF THE INVENTION

Field of the Invention

The present patent application is generally related to surgical procedures, and is more specifically related to systems, devices and methods for testing the performance of sutures that are used to close surgical openings and wounds.

Description of the Related Art

During a surgical procedure, a surgical incision is made through the skin and/or soft tissue to facilitate an operation. In many instances, multiple surgical incisions may be necessary. Surgical incisions are typically made as small and unobtrusive as possible to facilitate safe and timely operating conditions and timely recovery and healing after the surgery.

At the conclusion of a surgical procedure, the surgical incisions must be closed. Over the years, many different techniques have been developed for closing surgical incisions. One widely used technique for closing surgical incisions involves using sutures. Typically, a needle is attached to an end of the suture, and the needle is drawn through tissue to form one or more loops that hold the tissue together. The suture is subsequently tied off in one or more knots so that the tissue remains drawn together.

Although sutures have proven to be very effective for closing surgical incisions, there are a number of issues associated with using conventional sutures. First, conventional sutures require the use of knots to secure the sutures in place. If the knots are not tied properly, defects may arise including slippage, knot breakage, re-opening of the surgical incision, and infections. Second, tying knots requires extra work and lengthens the time necessary to complete the surgery.

In response to the above-noted issues associated with using conventional sutures, barbed sutures have been developed. Unlike conventional sutures, barbed sutures have projecting barbs that allow the suture to be used to close surgical openings and wounds, approximate tissue, tighten tissue, and attach prosthetic devices—all without using knots. Barbed sutures achieve proper tensioning of the tissue and fixation by applying tension to the sutures. Thus, barbed sutures provide advantages over conventional sutures including the ability to achieve better closure of surgical openings and wounds, shortened operating times, and reduced costs.

Sutures are frequently used during orthopedic surgery, which is a branch of surgery concerned with acute, chronic, traumatic, and overuse injuries and other disorders of the musculoskeletal system. Orthopedic surgeries include hand surgery, shoulder and elbow surgery, foot and ankle surgery, spine surgery, and joint reconstruction (arthroplasty) such as knee replacement. These orthopedic procedures often require the use of specialized surgical instruments to treat relatively softer musculoskeletal tissue (e.g., muscle, tendons, ligaments) and relatively harder musculoskeletal tissue (e.g., bone).

Knee replacement surgery, also known as knee arthroplasty, is a surgical procedure that replaces the weight-bearing surfaces of the knee joint to relieve pain and/or disability. Knee replacement surgery can be performed as a partial or a total knee replacement.

Knee replacement surgery typically involves exposing the front of the knee and detaching part of the quadriceps muscle from the patella. The patella is displaced to one side of the knee joint, which exposes the distal end of the femur and the proximal end of the tibia. The ends of these bones are then accurately cut to shape using cutting guides oriented to the long axis of the bones. In many instances, the cartilage and the anterior cruciate ligament are removed. The posterior cruciate ligament may also be removed but the tibial and fibular collateral ligaments are preserved. Metal components are then impacted onto the bone or fixed using fixing methodologies such as cement and cement-less techniques (e.g., osseointegration).

Knee replacement surgery typically results in substantial postoperative pain, and recovery may require vigorous physical therapy. The post-operative recovery period may be six weeks or longer and may involve the use of mobility aids (e.g. walking frames, canes, crutches, continuous passive motion machines, etc.) to enable the patient to return to preoperative mobility.

There are many risks and complications linked with knee replacement surgery, which are similar to those associated with all joint replacement surgeries. The most serious complication is infection of the joint (e.g., surgical site infection), which occurs in <1% of patients. Risk factors for infection are related to both patient and surgical factors.

Wound related complications, and in particular wound drainage, is an important factor that can increase the risk of surgical site infection (SSI) and/or periprosthetic joint infection (PJI) following knee replacement surgery and/or total joint arthroplasty (TJA).

In view of the above, there remains a need for surgical systems, devices, and methods that provide a watertight closure of the arthrotomy and sealed soft tissue closure, which is important to avoid wound complications (e.g., infections) after total knee replacement (i.e., total knee arthroplasty—TKA). There also remains a need for systems, devices and methods of testing the different types of sutures that may be used during joint arthroplasties to close surgical openings in order to select those types of sutures that will best minimize complications (e.g., infection) and promote rapid healing and recovery.

SUMMARY OF THE INVENTION

As noted above, wound related complications, and in particular wound drainage, is an important factor that can increase the risk of surgical site infection (SSI) and/or periprosthetic joint infection (PJI) following total joint arthroplasty (TJA). Thus, a watertight closure of the arthrotomy and sealed soft tissue closure is essential to avoid wound complications after total knee arthroplasty (TKA).

In one embodiment, systems, devices and methods are disclosed for testing and evaluating the integrity and performance of sutures that are used to close surgical openings and/or wounds that may be formed during total knee arthroplasty (TKA). In one embodiment, the systems, devices, and methods disclosed herein preferably enable medical personnel and engineers to consistently and reliably evaluate the integrity of capsule closure and soft tissue closure following TKA to better understand the safety, strength, utility, and performance of sutures such as barbed sutures.

In one embodiment, systems, devices and methods are used for evaluating the arthrotomy soft tissue closure following surgery under conditions of static pressurization, articulation, and breakage of the closure mechanics (e.g., sutures).

In one embodiment, a system for testing sutures preferably includes a test bench, a framework supporting the test bench above a surface, and a continuous passive motion (CPM) machine mounted on the test bench. The CPM machine is preferably configured to rotate between a first position in which the CPM machine is upright and located above the test bench and a second position in which the CPM machine is inverted and located below the test bench.

In one embodiment, the system includes a fluid supply subsystem for directing a fluid toward the CPM machine. In one embodiment, the system may include a fluid collection tray located below the test bench.

In one embodiment, the system preferably includes a support rod secured to and extending across an upper end of the framework, whereby the test bench includes a table that is rotatably mounted to the support rod.

In one embodiment, the CPM machine is secured to the table, whereupon the table and the CPM machine are configured to move together between the first position in which the CPM machine is upright and the second position in which the CPM machine is inverted.

In one embodiment, the framework includes spaced legs that extend vertically away from the surface. In one embodiment, the table lies in a plane that is parallel to the surface and perpendicular to longitudinal axes of the respective spaced legs.

In one embodiment, the fluid supply subsystem preferably includes a fluid feed container, a fluid tube having a first end connected with the fluid feed container and a second end spaced from the first end, and an infusion cannula coupled with the second end of the fluid tube.

In one embodiment, the fluid supply subsystem may include an elevating mechanism coupled with the fluid feed container for selectively raising and lowering the fluid feed container relative to a height of the test bench.

In one embodiment, the fluid supply subsystem may include a pump for circulating the fluid in the fluid supply subsystem. In one embodiment, the fluid supply subsystem may include a heat exchanger for heating the fluid in the fluid supply subsystem.

In one embodiment, the system may include a pressure monitoring subsystem coupled with the fluid supply subsystem for monitoring a pressure level of the fluid.

In one embodiment, the pressure monitoring subsystem may include a pressure monitoring catheter having a proximal end and a distal end, and a pressure sensor disposed at the distal end of the pressure monitoring catheter. In one embodiment, the distal end of the pressure monitoring catheter passes through the infusion cannula.

In one embodiment, the CPM machine may include an upper leg support having an upper leg clamp, a lower leg support having a lower leg clamp, and an articulating joint interconnecting the upper and lower leg supports for enabling the upper and lower leg supports to pivot relative to one another for extending and flexing the CPM machine.

In one embodiment, a cadaver leg is secured to the CPM machine. In one embodiment, the cadaver leg has a knee with a capsule that is aligned with the articulating joint of the CPM machine. In one embodiment, the infusion cannula passes through the capsule of the knee for establishing fluid communication between the fluid tube and an intracapsular cavity of the knee for infusing the fluid into the intracapsular cavity.

In one embodiment, the upper leg clamp secures an upper part of the cadaver leg to the upper leg support of the CPM machine and the lower leg clamp secures a lower part of the cadaver leg to the lower leg support of the CPM machine.

In one embodiment, the capsule of the knee of the cadaver leg has a surgical opening formed therein that is closed by one or more sutures.

In one embodiment, a system controller is in communication with the pressure sensor for monitoring a pressure level of the fluid infused into the intracapsular cavity of the knee.

In one embodiment, the elevating mechanism may include a winch having a winch cable wound about a spool, the winch cable having a free end that is coupled with the fluid feed container, and a winch handle coupled with the spool for selectively rotating the spool. In one embodiment, the winch handle is moveable in a first direction for raising the fluid feed container and is moveable in a second direction for lowering the fluid feed container.

In one embodiment, the pressure level of the fluid infused into the intracapsular cavity is increased by raising the fluid feed container and the pressure level of the fluid infused into the intracapsular cavity if reduced by lowering the fluid feed container.

In one embodiment, a system for testing sutures preferably includes a test bench including a rotatable table, a framework supporting the test bench and the rotatable table above a surface, and a continuous passive motion (CPM) machine mounted on the rotatable table. In one embodiment, the CPM machine is configured to rotate between a first position in which the CPM machine is upright and located above the rotatable table and a second position in which the CPM machine is inverted and located below the rotatable table.

In one embodiment, the system may include a fluid supply subsystem for directing an infusion fluid toward the CPM machine, a pump for circulating the infusion fluid in the fluid supply subsystem, a heat exchanger for heating the infusion fluid, a fluid collection tray located below the CPM machine and the rotatable table, and a pressure monitoring subsystem for monitoring a pressure level of the infusion fluid.

In one embodiment, the CPM machine may include an upper leg support, a lower leg support, and an articulating joint interconnecting the upper and lower leg supports for enabling the upper and lower leg supports to pivot relative to one another for extending and flexing the CPM machine.

In one embodiment, the CPM machine may have a motor for moving the upper and lower leg supports between the extended and flexed configurations.

In one embodiment, a cadaver leg is positioned on the CPM machine. In one embodiment, the cadaver leg has a knee with a capsule that is aligned with the articulating joint of the CPM machine.

In one embodiment, the fluid supply subsystem includes a fluid feed container, an infusion fluid tube having a first end connected with the fluid feed container and a second end spaced from the first end, and an infusion cannula coupled with the second end of the infusion fluid tube. In one embodiment, the infusion cannula preferably passes through the capsule of the knee for establishing fluid communication between the infusion fluid tube and an intracapsular cavity of the knee.

In one embodiment, the pressure monitoring subsystem preferably includes a pressure monitoring catheter having a proximal end and a distal end, and a pressure sensor disposed at the distal end of the pressure monitoring catheter. In one embodiment, the distal end of the pressure monitoring catheter desirably passes through the infusion cannula and into the intracapsular cavity of the knee for monitoring the pressure level of the infusion fluid disposed within the intracapsular cavity.

In one embodiment, the fluid supply subsystem may have an elevating mechanism coupled with the fluid feed container for selectively raising and lowering the fluid feed container relative to a height of the test bench. In one embodiment, the pressure level of the infusion fluid is increased by raising the fluid feed container relative to the height of the bench and the pressure level of the infusion fluid is reduced by lowering the fluid feed container relative to the height of the bench.

In one embodiment, a method of testing the performance of sutures desirably includes providing a test bench having a rotatable table configured to rotate between an upright configuration and an inverted configuration, and securing a continuous passive motion (CPM) machine to the rotatable table. The CPM machine may have an upper leg support, a lower leg support, and an articulating joint interconnecting the upper and lower leg supports for enabling the upper and lower leg supports to pivot relative to one another for extending and flexing the CPM machine.

In one embodiment, with the rotatable table and the CPM machine in the upright configuration, a cadaver leg having a surgical opening closed by one or more sutures may be positioned on the CPM machine with an upper part of the cadaver leg secured to the upper leg support, a lower part of the cadaver leg secured to the lower leg support, and a knee of the cadaver leg aligned with the articulating joint of the CPM machine.

In one embodiment, a method includes infusing fluid into an intracapsular cavity of the knee of the cadaver leg, and after the infusing fluid step, activating a motor of the CPM machine for continuously flexing and extending the cadaver leg through a range of motion.

In one embodiment, a method includes rotating the rotatable table and the CPM machine into the inverted configuration so that the cadaver leg is inverted and located below the rotatable table, and, after the rotating step, collecting any of the infused fluid that passes through the surgical opening closed by the one or more sutures.

In one embodiment, the method may include increasing a pressure level of the fluid infused into the intracapsular cavity of the cadaver leg, and monitoring the pressure level of the fluid infused into the intracapsular cavity of the cadaver leg.

In one embodiment, the system provides a constant pressure infusion system that measures the leak rate of the suture line for a given capsule pressure. The constant pressure system allows the intracapsular pressure to be accurately adjusted independent of the leak and held constant for the duration of a test.

In one embodiment, the system preferably includes a rapid, high-volume heat exchanger. In one embodiment, the temperature of the infusion liquid is kept constant. In one embodiment, the heat exchanger matches the fluid temperature in humans to maintain similar in-vivo conditions.

In one embodiment, the pressure monitoring subsystem preferably includes a pressure transducer that is located within the capsule under the suture line. In one embodiment, the efficacy of a watertight closure of the knee capsule is assessed by monitoring the amount of fluid leakage. In one embodiment, the driving force of leakage is the pressure. The system includes systems for controlling and correcting fluid pressure to enhance accuracy and measurement.

In one embodiment, the system includes adjustable leg clamps that are used for securing leg specimens into a CPM machine. The leg clamps preferably secure the leg into the CPM machine while the machine flexes to make sure the joint is moving properly and keeps the leg in place when the table is inverted.

In one embodiment, when fluid is infused into the capsule for testing sutures, high pressures are generated within the capsule as the knee is flexed due to a reduction in space. The high pressure can produce hydro-dissection of the soft tissue when the infused fluid is forced into the upper and lower leg. In order to avoid the above-mentioned problems, in one embodiment, the adjustable leg clamps may act as a tourniquet. In one embodiment, the leg clamps preferably squeeze the upper and lower regions about the knee, thereby preventing any of the water infused into the capsule to migrate into the tissue in the thigh or calf.

In one embodiment, the framework that supports the rotatable table and the CPM machine is preferably rigid. In one embodiment, the framework is an extruded aluminum base frame that is fabricated to provide a rigid heavy experimental base to eliminate any motion artifact into the measurements.

In one embodiment, rotating the CPM machine and the leg into the inverted position avoids problems that may result from air being trapped inside the intracapsular cavity so that any trapped air will go to the back of the leg thereby insuring that the infused fluid is against the suture line.

In one embodiment, inverting the leg facilitates closure leakage assessment because the collection of fluid is assisted by gravity through inversion of the leg.

In one embodiment, the system may include video capture and source lighting. In one embodiment, a video camera is integrated onto the moving rail of the CPM machine to allow a video camera the ability to image and project the knee, while upside down, onto a video monitor for observation and recording. In one embodiment, a dedicated light source may be secured to the moving rail of the CPM machine to maintain lighting throughout the full range of motion of the flex cycle.

In one embodiment, the systems, devices and methods disclosed herein solve many problems associated with measuring the leak rate of suture line closures as a function of capsule pressure and knee dynamics.

In one embodiment, a pressure sensor, such as a solid state micro-transducer may be located within the knee capsule and below the suture closure to allow for direct measurement of a fluid pressure level within the intracapsular cavity.

In one embodiment, suture closure performance for many different cadaver legs is tested and the pressure differences across the different suture lines must be consistent for each trial to be able to measure the leak rate as a function of pressure.

In one embodiment, in order to accurately measure the leak rate of the wound closure, the pressure within the capsule space must be the same for each specimen, independent of the closure.

In one embodiment, the system preferably allows for leak detection. In one embodiment, the system is designed to invert the leg, allowing the leakage from the suture line to drip off the surface of the knee into a collection tray. The system disclosed herein provides a dramatic improvement over prior art systems and methodologies that collect fluid that is running down the side of the leg by blotting or suction. In the prior art systems and methods, fluid is easily missed, leading to errors associated with the leak collection.

If the knee is tested when in an upright position, the closure of the knee results in unwanted air lying against the suture line, blocking the water and preventing the defect from leaking. In one embodiment, inverting the leg being tested allows any residual air to move to the back of the capsule and the water present in the capsule to lie against the suture line, ensuring an accurate assessment of leakage from each specimen.

In one embodiment, the circular knife penetrates the capsule wall from the outside of knee in, and the insertion tool is pushed forward into the capsule space. After the circular knife is removed from the end of the insertion tool, the infusion cannula is inserted from inside of capsule over the insertion tool and guided through the opening formed by the circular knife in the capsule wall. In one embodiment, the retaining collar is placed over the cannula, cinched down to the capsule tissue and secured in place with the set screw.

In one embodiment, a system for testing suture performance for human knee watertight capsule closure preferably includes multiple subsystems.

In one embodiment, the system for testing suture performance preferably includes a continuous passive motion (CPM) machine, which is a physical therapy system used by a patient after surgery to aid in wound healing and recovery.

In one embodiment, the system for testing suture performance preferably includes an inversion table designed to invert a cadaver leg during testing to provide precise collection of the water leakage from the knee closure (e.g., the suture line).

In one embodiment, the system for testing suture performance preferably includes a constant pressure gravity fed water infusion system that is designed to provide water to a knee capsule for pressure testing of the wound closure for evaluating suture performance.

In one embodiment, the system for testing suture performance preferably includes a heat exchanger configured to heat the infusion fluid for replicating the body temperature of a human.

In one embodiment, the system for testing suture performance preferably includes an infusion cannula designed to provide a leak free structure for infusing and/or introducing water into a knee capsule having a wound that has been closed using sutures.

In one embodiment, the infusion cannula desirably provides a passageway for an intracapsular pressure transducer that is configured to monitor the pressure level of the fluid infused into the capsule.

In one embodiment, the system preferably includes a computer integrated pressure measurement system configured to measure and digitally record the pressure within the knee capsule for applied stress to the closure.

In one embodiment, the system preferably includes a water collection and measurement system that is configured to collect the fluid that leaks from the wound and/or suture line to precisely weigh the volume of the fluid that leaks past the suture line.

In one embodiment, the tissue that is used for testing the performance of sutures is prepared for testing. In one embodiment, each cadaver leg is removed from a freezer, unboxed, left wrapped as shipped, and allowed to thaw at room temperature for a minimum of 48 hours prior to commencing a study.

In one embodiment, prior to performing surgery on a cadaver leg, the thigh and foot are wrapped with absorbent padding. The temperature of the leg is measured at a site located within the thigh muscle near the femur head.

In one embodiment, the same surgeon will perform all of the arthrotomies and closures to minimize procedural variations among trials. Prior to execution of the study, the surgeon is preferably familiar with the use of both the control suture (e.g., the VICRYL suture) and the test suture (e.g., the STATAFIX suture).

In one embodiment, the leg is placed on a surgical table in a dorsal recumbent position in 30 degrees flexion.

In one embodiment, a skin incision of approximately 20 cm is made over the patella and down to the level of the subcutaneous fat layer.

In one embodiment, the skin and subcutaneous fat are blunt dissected off the anterior aspect of the knee and cut away to enhance visualization of the suture closure throughout testing.

In one embodiment, a standard mini-medial parapatellar arthrotomy is performed using a Number 10 scalpel blade with the knee in 30 degrees of flexion extending from 3 cm proximal to the superior pole of the patella to the proximal medial aspect of the tibial tubercle.

In one embodiment, the knee capsule is flushed with distilled water via a bulb syringe and suction to remove residual synovial fluid.

In one embodiment, an infusion cannula and a pressure transducer are placed within a knee capsule.

In one embodiment, the infusion cannula is secured (e.g., pinned) to the capsule wall and has a design that insures that the pressure transducer is not blocked by tissue potentially preventing a true pressure measurement of the water inside the capsule. In one embodiment, the infusion cannula and pressure transducer are preferably inserted into the intracapsular cavity in the suprapatellar pouch of the knee using a trocar with a circular knife to create a small hole. The infusion cannula is placed from inside out and secured to the tissue wall. The cannula may be secured to the tissue wall using a retaining ring that slides over a stem of the infusion cannula and/or by using a purse string suture. In one embodiment, a surgical adhesive such as the adhesive sold by Johnson & Johnson Corporation on New Brunswick, N.J. under the trademark DERMABOND® may be used to repair leaks around the cannula.

In one embodiment, a template may be used to mark the site of each needle penetration to standardize the suture placement between specimens. In one embodiment, the bites for the suture needle penetration are preferably about 8 mm apart and 6 mm from the incision edge.

In one embodiment, closure of the arthrotomy (i.e., joint capsule) is performed with the leg at 30 degrees of flexion.

Test Group Closure. In one embodiment, the test group closure is performed using STRATAFIX® Symmetric PDS™ Plus size 1 with a CT-1 needle using a continuous closure pattern. The edge of the tissue is preferably everted during needle passage to ensure a full wall thickness passage of the needle with the synovial membrane captured in each pass. Before closure of the last few centimeters of the arthrotomy, water (e.g., warm distilled water) is preferably flushed through the infusion cannula to de-air the capsule of any residual air.

Control Group Closure. In one embodiment, control group closure is performed using VICRYL® size 1 with a CT-1 needle using an inverted figure-8 interrupted suture pattern where the crossover point occurs in the capsule as opposed to on the tissue surface. Before closure of the last few centimeters of the arthrotomy, warm distilled water is preferably flushed through the infusion cannula to de-air the capsule of any residual air. The edge of the tissue is preferably everted during needle passage to ensure a full wall thickness passage of the needle with the synovial membrane captured in each pass. In one embodiment, before closure of the final centimeter of the arthrotomy, the infusion catheter will preferably have normal saline flushed through the knee to remove residual air.

Marker suture for suture release testing. In one embodiment, small marker sutures (e.g., green marker sutures) may be attached mid-wall near the closure loops to identify a midpoint suture to be cut during the suture release phase of testing. Alternatively, in one embodiment, the suture loop to be cut may be identified with skin marker or tissue marking dye. For wound closures having even numbered sutures, the loop to be cut is preferably the loop that is immediately distal to the midline.

Minimizing Tissue Weeping. In one embodiment, laparotomy pads may be secured to the leg prior to testing. In one embodiment, sutures may be used for securing the laparotomy pads in place.

Continuous Passive Motion (CPM) Machine. In one embodiment, after completion of the capsule closure, the leg is transferred to the CPM machine secured to the rotatable table.

Prior to placing the leg in the CPM machine, the assemblies of the machine that support the thigh and calf of the leg are preferably adjusted to accommodate the length dimensions of the leg specimen. The length of the thigh is measured from the greater trochanter to the center of the knee joint. The thigh section of the CPM machine is adjusted to this length. The length of the calf is measured from the center of the knee to the bottom of the foot. The calf section of the CPM machine is adjusted to this length.

In one embodiment, foam padding may be placed within the leg clamps of the CPM machine.

In one embodiment, a surgical drape may be placed over the CPM machine and the leg lowered into the CPM machine.

In one embodiment, the leg is positioned in the CPM machine and the foot strap is tightly secured around the foot. The knee joint is aligned with the articulation joint of the CPM machine. If the leg is not properly aligned, the CPM machine is adjusted so that the length of the calf and thigh frame components properly accommodates the leg. The leg and thigh clamps are preferably secured around the leg.

Arthrotomy Closure Testing. In one embodiment, the water tight condition of the knee joint is assessed by infusing water (e.g., distilled water) into the joint capsule from a gravity feed constant pressure system.

Constant Pressure Gravity Feed Infusion System. In one embodiment, a fluid feed container is lowered to a height below the infusion point of the knee and the infusion fluid tube is clamped off with a tubing clamp.

In one embodiment, a roller pump and a water bath are turned on to pre-heat the fluid in the fluid feed container to approximately 37 degrees Celsius.

In one embodiment, barbed sutures provide a secure, watertight retinacula closure in a cadaveric model. In one embodiment, the barbed sutures are manufactured by cutting into the core of the suture to create the barbs. In one embodiment, the barbed sutures have anchors that are formed as a part of the core, providing substantial strength. In one embodiment, the barbed sutures are sold by Johnson & Johnson Corporation of New Brunswick, N.J. under the trademark STRATAFIX® Symmetric PDS™ Plus Knotless Tissue Control Device.

In one embodiment, human cadaver fresh-frozen legs that have no history of violation on the soft tissue about the knee (i.e. prior surgery, trauma, tumor, or inflammatory arthritis) are used. In one embodiment, donor criteria for the cadaver legs may include age: 25-65, weight 140-190 lbs., height 60-74 inches, and BMI greater than 18.5.

In one embodiment, the right and left legs of 10 donors (20 legs) are randomized to either a control group using barbless sutures (e.g., VICRYL® sutures) or a test group using barbed sutures (e.g., STRATAFIX™ sutures) using an "out of the hat" randomization scheme with the contralateral leg assigned to the other group. The leg samples that are used preferably extend from the femur head to the foot.

In one embodiment, a study is designed so that only donors with two acceptable legs are admitted, such that one leg will receive barbed sutures and the other leg will receive barbless sutures. This design strategy allows for paired testing to minimize potential individual differences in soft tissue related issues.

If, during surgery, an unknown physical abnormality is identified or a technical error arises during the arthrotomy, suturing, or experimentation that cannot be repaired or overcome, the leg and the contralateral leg will be omitted from the study, and a new leg will be selected randomly from sets of cadaver legs that match predetermined testing criteria.

These and other embodiments of the present patent application will be described in more detail below.

BRIEF DESCRIPTION OF THE DRAWINGS

FIG. 32 is a top perspective view of an infusion cannula, a circular knife, and an insertion tool, whereby the circular knife and the insertion tool are used to insert the infusion cannula into the capsule of a knee for infusing fluid into the capsule, in accordance with one embodiment of the present patent application.

FIG. 33 shows the infusion cannula and the circular knife of FIG. 32 after being coupled with the insertion tool of FIG. 32, in accordance with one embodiment of the present patent application.

FIG. 34A shows a first step of a method of inserting an infusion cannula into the capsule of a knee, in accordance with one embodiment of the present patent application.

DETAILED DESCRIPTION OF PREFERRED EMBODIMENTS

Figure 1:
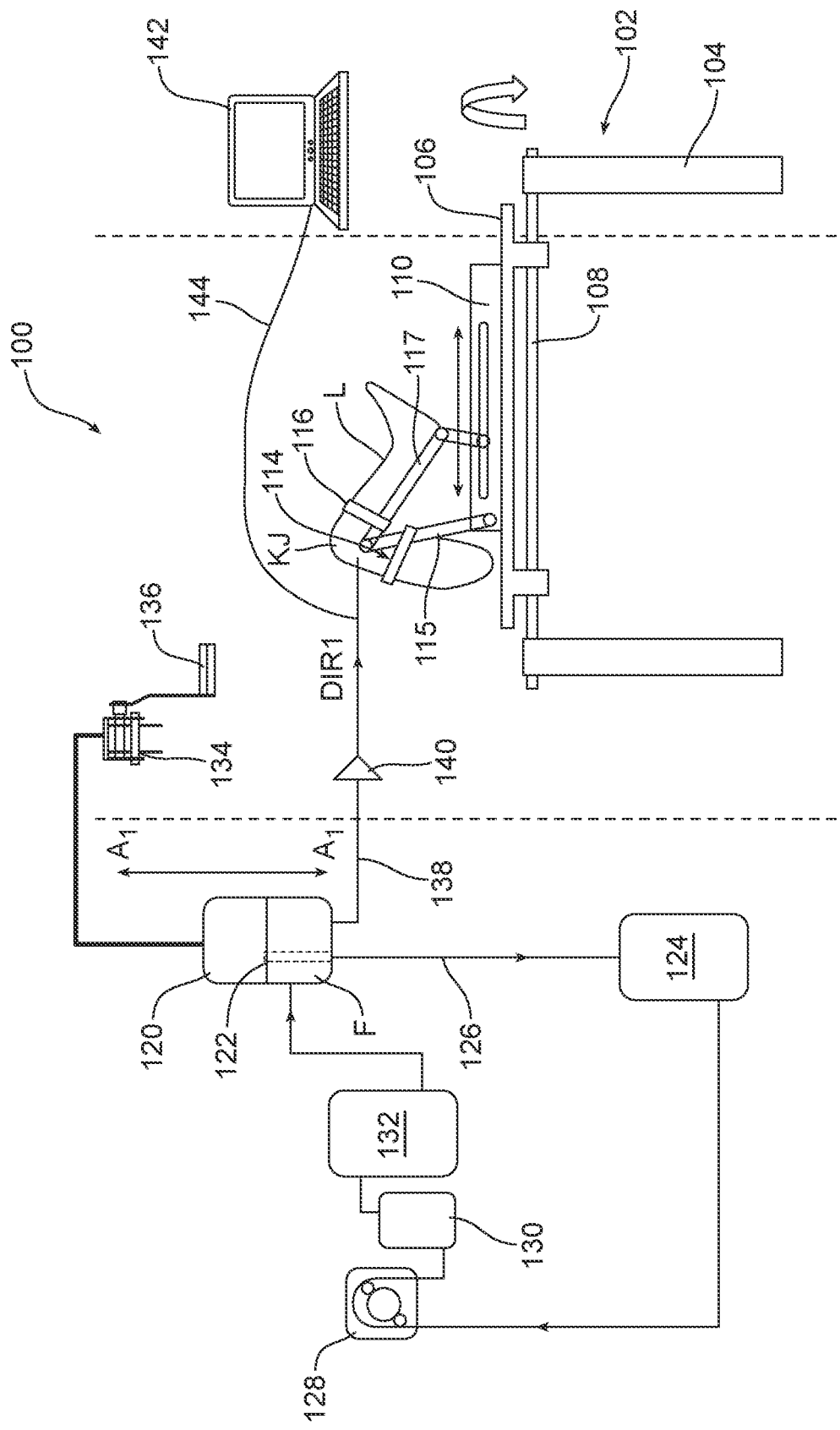
FIG. 1 is a schematic view of a system for testing suture performance, in accordance with one embodiment of the present patent application.

Referring to FIG. 1, in one embodiment, a system 100 for testing suture performance preferably includes a test bench 102 having a support base 104 and a rotatable table 106 that is mounted on a support rail 108. In one embodiment, the rotatable table 106 is rotatably coupled with the support rail 108. In one embodiment, the ends of the support rail 108 are secured with an upper end of the test bench 102.

In one embodiment, the system 100 preferably includes a continuous passive motion (CPM) machine 110 that is mounted on the rotatable table 106. The CPM machine 110 preferably includes an articulating joint 112, a first leg clamp 114 that is adapted to secure an upper leg of a leg L to an upper leg support 115, and a second leg clamp 116 that is adapted to secure a lower leg of the leg L to a lower leg support 117. In one embodiment, the CPM machine 110 may be operated to continuously move the leg L over a range of motion between an extended position and a flexed position. In one embodiment, the CPM machine may be similar to the machines sold by DJO, LLC of Vista, Calif. under the trademark OPTIFLEX-K1®. https://www.djoglobal.com/products/chattanooga/optiflex-k1.

In one embodiment, the system 100 preferably includes a fluid supply subsystem 118 that is configured to infuse fluid (e.g., water, distilled water) inside an articular capsule of the knee K of the leg L. The articular capsule of the knee joint (commonly referred to as the capsular ligament) contains the patella ("knee cap"), ligaments, menisci, and bursae. The articular capsule, hereinafter referred to as the capsule or knee capsule, includes a synovial and a fibrous membrane separated by fatty deposits anteriorly and posteriorly. In one embodiment, the fluid supply subsystem 118 preferably includes a fluid feed container 120 having a spillway valve 122 that functions to maintain a predetermined, constant fluid level and/or fluid volume within the fluid feed container 120. If excess fluid is in the fluid feed container 120, the excess fluid will flow through the spillway valve 122 until the fluid level returns to the predetermined, constant fluid level.

In one embodiment, the fluid supply subsystem 118 desirably includes a fluid reservoir 124 that contains a source of fluid that is utilized by the system 100. A first fluid conduit 126 preferably extends between the spillway valve 122 of the fluid feed container 120 and the fluid reservoir 124, whereby any excess fluid that is disposed inside the fluid feed container 120, which is above the upper end of the spillway valve 122, will pass through the first fluid conduit 126 for being stored in the fluid reservoir 124.

The fluid supply subsystem 118 desirably includes a fluid pump 128, a heat exchanger 130 and a compliance chamber 132 that is located upstream from the fluid feed container 120. In one embodiment, the fluid pump 128 draws fluid from the fluid reservoir 124 and directs the drawn fluid through the heat exchanger 130 to heat the fluid to a temperature that is compatible with the temperature of a human body (e.g., 37 degrees Celsius). In one embodiment, the compliance chamber 132 evaluates the heated fluid that is discharged from the heat exchanger 130 to insure that the fluid complies with predetermined specification requirements prior to feeding the fluid into the fluid feed container 120.

In one embodiment, the fluid feed container 120 may be raised and lower along an axis $A_1$ by utilizing a winch 134 having a rotatable winch handle 136. In one embodiment, the pressure of the fluid F supplied by the fluid feed container 120 may be increased by utilizing the winch 134 to raise the height of the fluid feed container 120. In one embodiment, the pressure of the fluid supplied from the fluid feed container 120 may be lowered by using the winch 134 to lower the fluid feed container 120. Thus, the pressure level of the fluid may be raised or lowered by raising and lowering the fluid feed container.

In one embodiment, an infusion fluid tube 138 desirably extends between the fluid feed container 120 and an infusion cannula that is inserted into the capsule of the knee K of the leg L. The infusion fluid tube 138 desirably includes a one-way check valve 140 that enables the fluid from the fluid feed container 120 to flow in only one direction designated DIR1, namely, from the fluid feed container 120 to the infusion cannula inserted into the capsule of the knee K.

In one embodiment, the system 100 for evaluating the performance of sutures desirably includes a system controller 142. In one embodiment, the system controller 142 may include one or more computers having one or more microprocessors and one or more software programs for monitoring and controlling the operation of the testing system 100. In one embodiment, the system controller 142 may be coupled with a pressure transducer 144 that passes through the infusion fluid tube 138 and an infusion cannula for being disposed inside the capsule of the knee K. The pressure transducer 144 preferably continuously records the pressure level of the fluid that is infused into the capsule of the knee so that the pressure levels may be monitored, recorded, and evaluated by the system controller 142. In one embodiment, the components of the subsystem that monitors pressure levels within the capsule of the knee may include a system sold by BIOPAC Systems, Inc. of Goleta, Calif. under the trademark MP150 System (https://www.biopac.com/products/?fwp_product_search=MP150 system); and a pressure catheter sold by Millar, Inc. of Houston, Tex. under the trademark Millar Mikro-Cath™ Pressure Catheter (https://millar.com/clinical/products/mikro-cath).

Figure 2:
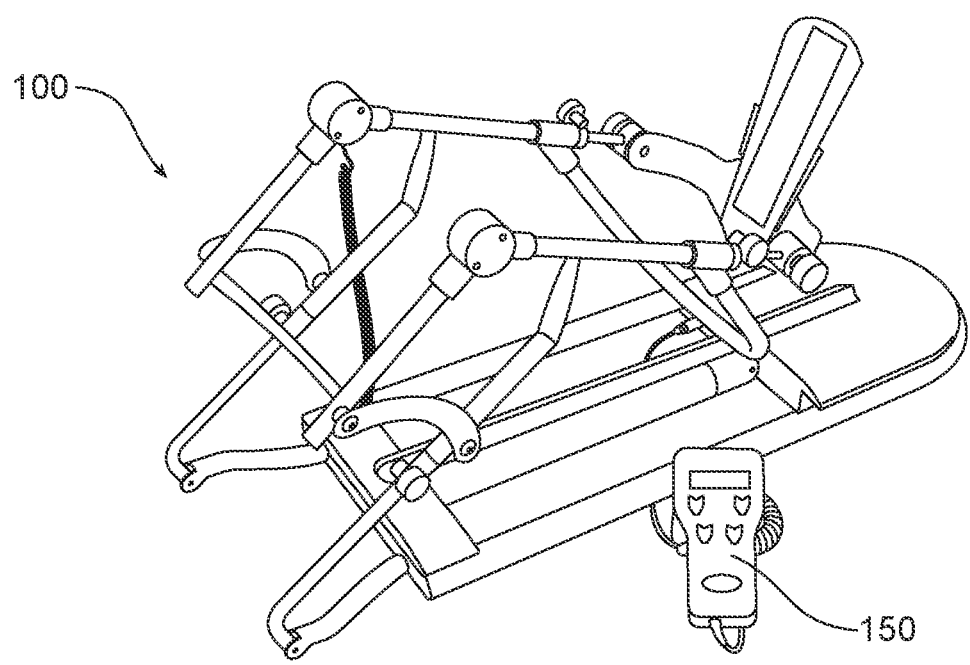
FIG. 2 is a perspective view of a continuous passive motion (CPM) machine that is incorporated into the system shown in FIG. 1, in accordance with one embodiment of the present patent application.

Referring to FIG. 2, in one embodiment, the system 100 (FIG. 1) for evaluating the performance of sutures preferably includes the continuous passive motion (CPM) machine 110, which is configured to receive a cadaver leg having a surgical opening that has been closed using sutures. In one embodiment, the surgical opening may be formed in a capsule of a knee of a cadaver leg. In one embodiment, the leg may be secured to the CPM machine 110, whereby the CPM machine will move the secured leg between extended and flexed positions for evaluating the performance of the sutures that have been used to close the surgical opening.

In one embodiment, the CPM machine 110 is similar to those that are used during the first phase of rehabilitation of knees following surgical procedures such as partial or total knee replacement surgeries. The CPM machine 110 preferably continuously moves a cadaver leg through a controlled range of motion whereby an operator may control the parameters of the range of motion and the speed at which the CPM machine moves the leg between the extended and flexed positions.

In one embodiment, the CPM machine 110 may include a controller 150 that enables an operator to select a range of motion and a frequency for moving a cadaver leg between the extended and flexed positions. For example, the controller 150 for the CPM machine 110 may be utilized to initially move a leg between 0 degrees (i.e., extended) and 45 degrees (i.e., partially flexed). After initial rehabilitation, the controller 150 may be engaged to increase the degree of flexing the leg from 45 degrees to 90 degrees or more. The controller 150 may also be utilized to monitor and adjust the frequency at which the CPM machine moves the leg between the extended and flexed position. For example, initial rehabilitation exercises may move the leg more slowly between extended and flexed position (e.g., one cycle per minute), while later rehabilitation exercises may move the leg between the extended and flexed positions at a greater frequency level (e.g., two or more cycles per minute).

Figure 3:
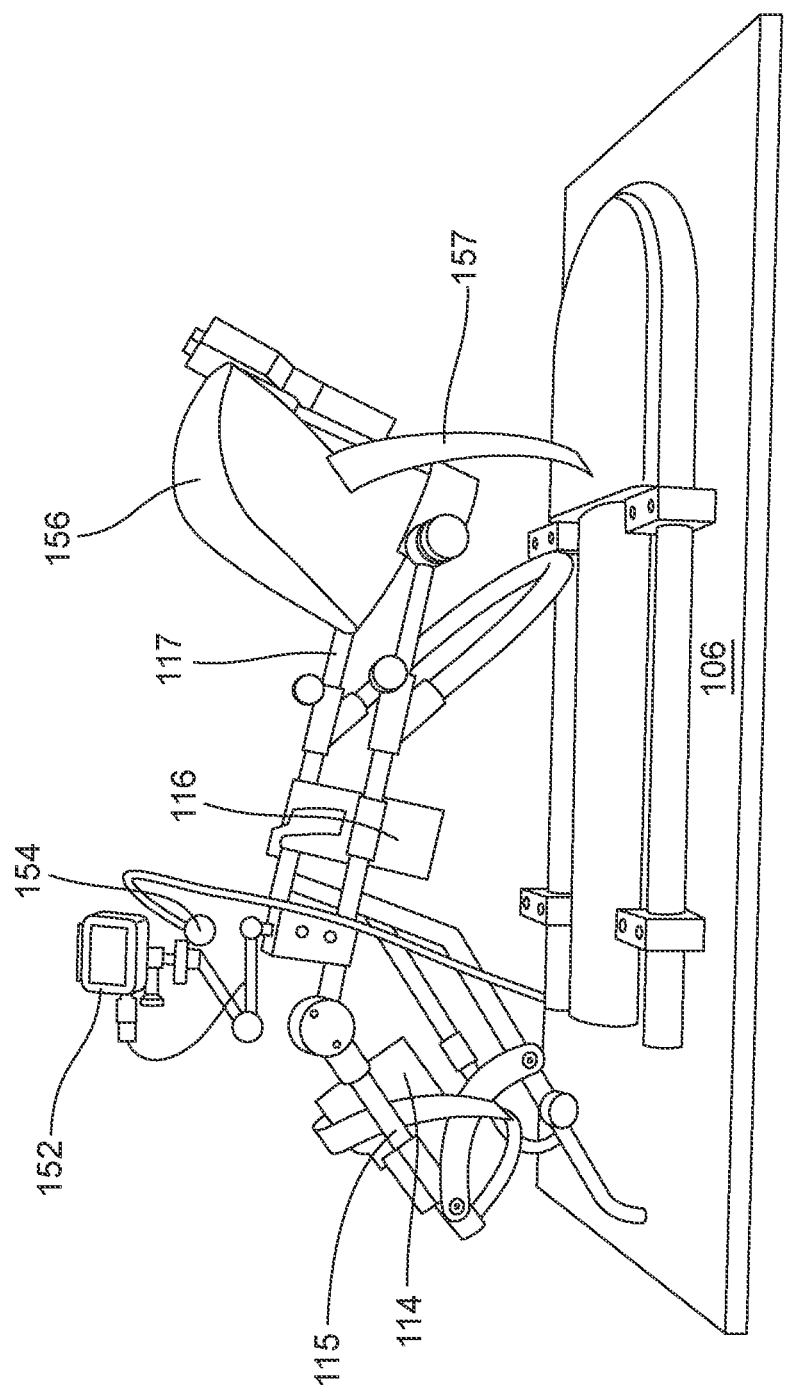
FIG. 3 is a side view of the CPM machine of FIG. 2 including a camera and a light source attached to the CPM machine, in accordance with one embodiment of the present patent application.

Referring to FIG. 3, in one embodiment, the CPM machine 110 may be mounted atop a rotatable table 106. In one embodiment, the rotatable table may be rotated between an upright position and an inverted position. In one embodiment, when the rotatable table 106 is in the upright position, the CPM machine 110 is preferably located above the table 106 and projects toward a ceiling of a room. In one embodiment, when the rotatable table 106 is rotated into an inverted position, the CPM machine 110 is preferably located below the table 106 and projects toward the floor of the room.

In one embodiment, the CPM machine 110 may include a camera 152 (e.g., a video recorder) that is adapted to record still and/or moving images of a cadaver leg that is secured to the CPM machine 110. In one embodiment, the system 100 for testing suture performance (FIG. 1) may also include a light source 154 that illuminates the knee joint so that the knee area of the cadaver leg is visible through the lens of the camera 152.

In one embodiment, the CPM machine 110 preferably includes a first leg clamp 114 that is utilized for clamping an upper leg region of a leg to the upper leg support 115, and a second leg clamp 116 that is utilized for clamping a lower leg region of the leg to the lower leg support 117. The first and second clamps 114, 116 are preferably tightened for holding the upper and lower leg regions to the CPM machine 110, with the knee of the leg being aligned with the articulating joint 112 of the CPM machine 110.

In one embodiment, the CPM machine 110 desirably includes a foot support 156 that is preferably adapted to secure a foot at the lower end of the leg for effectively securing the leg to the CPM machine 110. The system may include a securing strap 157 that is used to hold the foot in place inside the foot support 156. The securing strap 157 may include hook and loop fasteners.

Figure 4A:
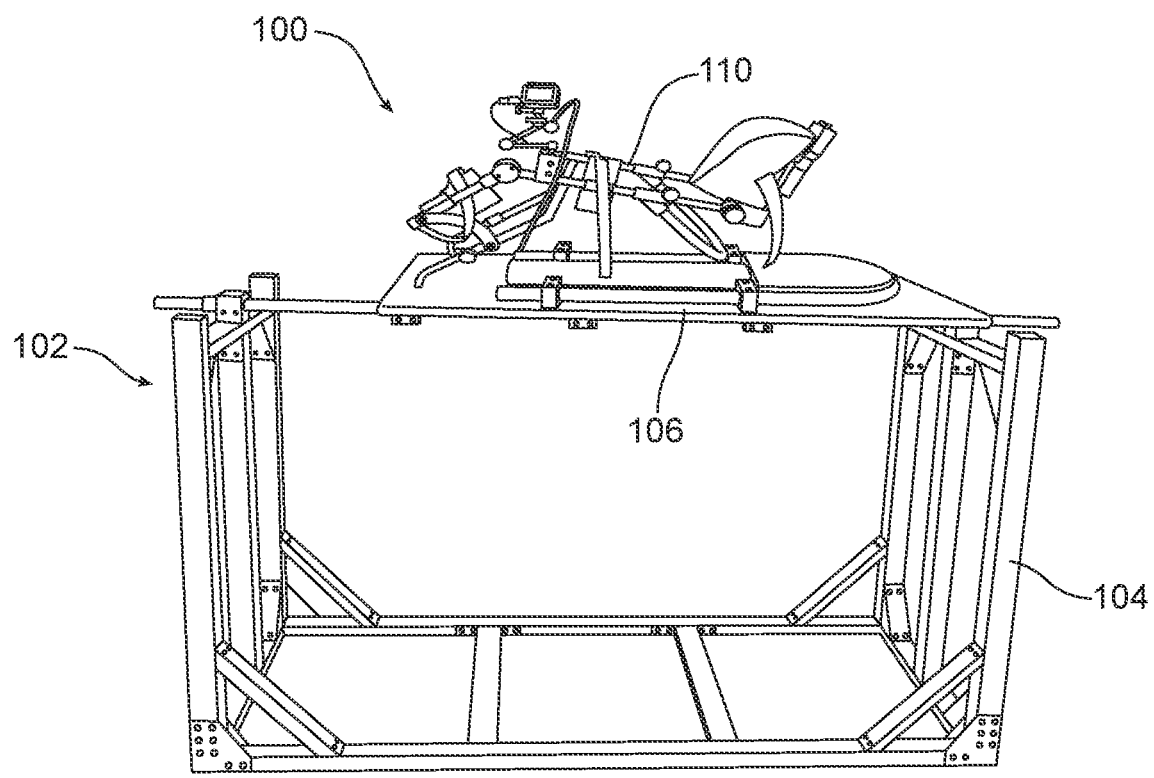
FIG. 4A is a side view of a system for testing the performance of sutures including a test bench having a rotatable table and a CPM machine secured to the rotatable table, in accordance with one embodiment of the present patent application.

Referring to FIG. 4A, in one embodiment, the system 100 for testing suture performance preferably includes the CPM machine 110, which is secured to the rotatable table 106, which, in turn, is coupled with the support rail 108 for enabling the rotatable table 106 to be rotated between upright and inverted positions. The outer ends of the support rail 108 are desirably coupled with the test bench 102. In one embodiment, the rotatable table 106 is rotatably coupled with the support rail 108 so that the rotatable table 106 may be selectively rotated between the upright and the inverted positions.

Figure 4B:
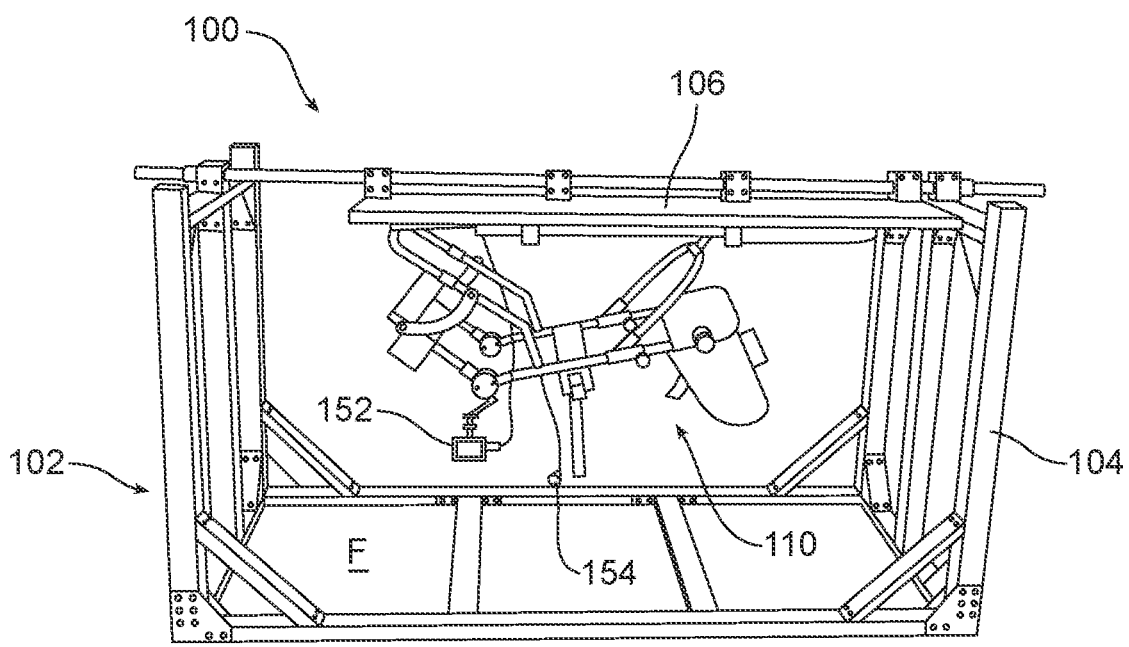
FIG. 4B is a side view of the system of FIG. 4A with the rotatable table and the CPM machine in an inverted position, in accordance with one embodiment of the present patent application.

FIG. 4A shows the rotatable table 106 in an upright position. FIG. 4B shows the rotatable table 106 after it has been inverted whereby the CPM machine 110 is located below the table 106 and projects toward the floor F of a room. The system may include a locking element or a biasing element for holding the table 106 in either the upright position (FIG. 4A) or the inverted position (FIG. 4B). The camera 152 and the light source 154 are desirably connected with the CPM machine 110 so that the camera 152 and light source 154 move with the CPM machine 110 as the CPM machine is rotated between the upright configuration shown in FIG. 4A and the inverted configuration shown in FIG. 4B. In FIG. 4B, the camera 152 and the light source 154 are located below the table 106.

Figure 5:
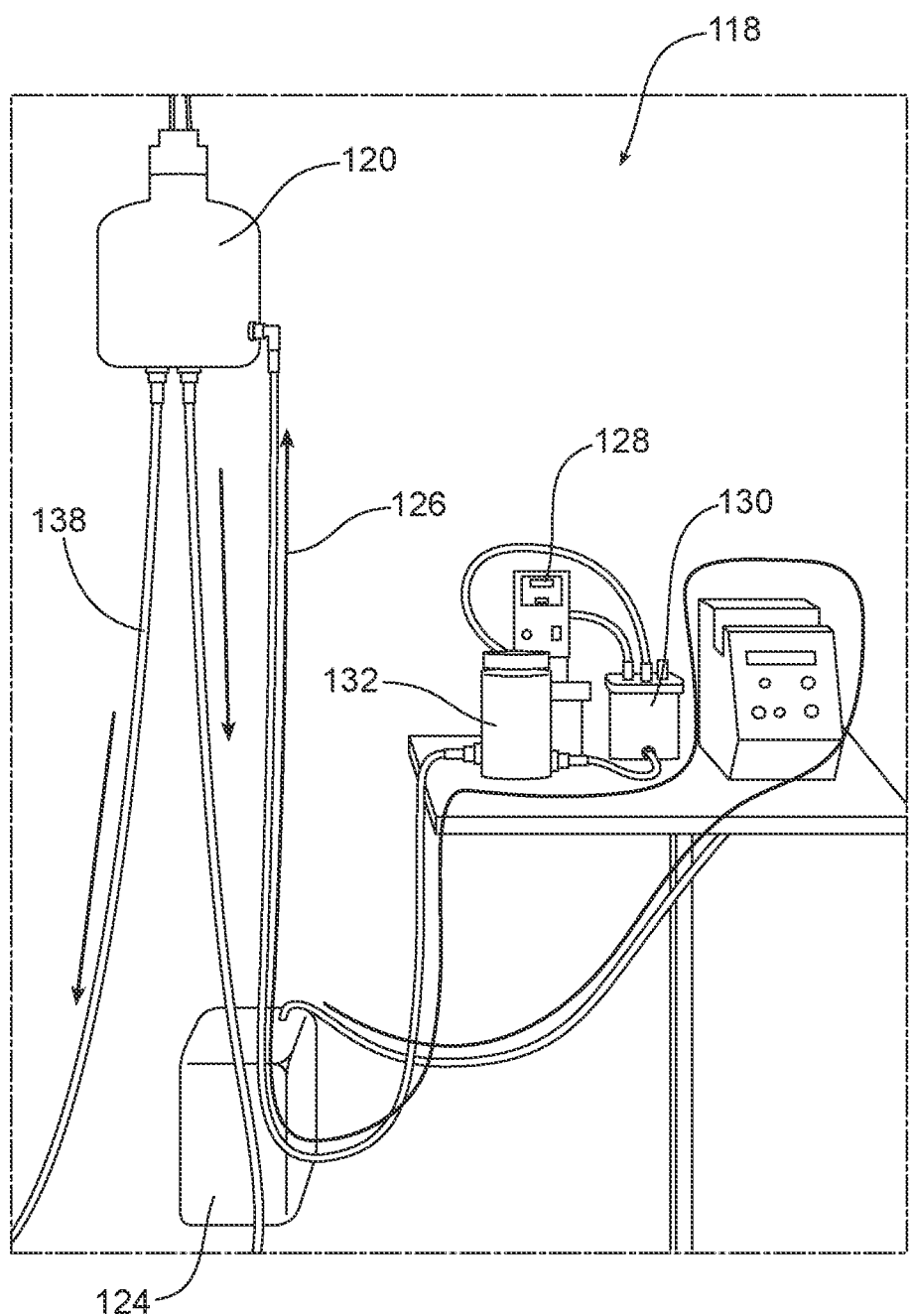
FIG. 5 shows a fluid supply subsystem for a system for testing suture performance, in accordance with one embodiment of the present patent application.

Referring to FIG. 5, in one embodiment, the system 100 (FIG. 1) for evaluating the performance of sutures preferably includes the fluid supply subsystem 118 that provides fluid that is infused into a capsule of a knee. In one embodiment, the fluid supply subsystem 118 preferably includes a fluid feed container 120 that is in fluid communication with a fluid pump 128 and a heat exchanger 130. In one embodiment, the heated fluid is passed through a compliance chamber 132 before it flows through the first fluid conduit 126 to the fluid feed container 120. Any excess fluid that is present in the fluid feed container 120 desirably flows into the fluid reservoir 124. The fluid feed container 120 is coupled with an infusion fluid tube 138 that supplies fluid to a capsule of a knee during a suture testing protocol that will be described in more detail herein.

Figure 6A:
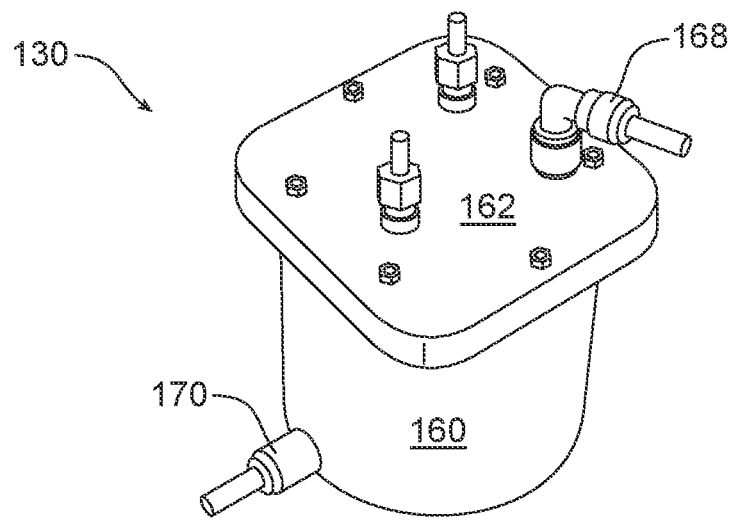
FIG. 6A is a perspective view of a heat exchanger for the fluid supply subsystem of FIG. 5, in accordance with one embodiment of the present patent application.
Figure 6B:
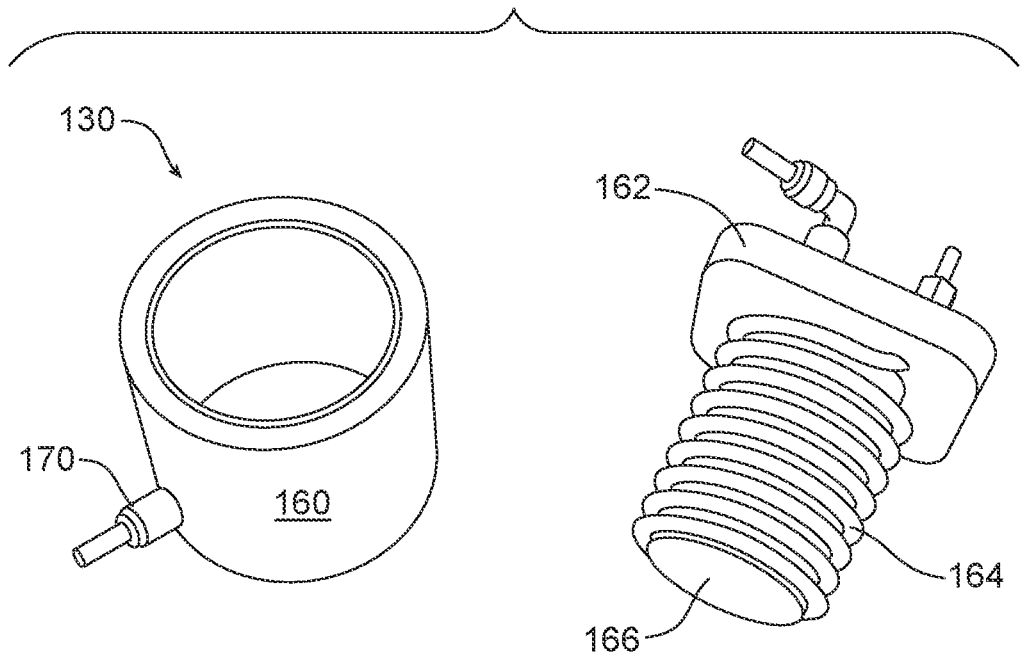
FIG. 6B is a perspective view of the heat exchanger of FIG. 6A with the components of the heat exchanger in an unassembled configuration, in accordance with one embodiment of the present patent application.

Referring to FIGS. 6A and 6B, in one embodiment, the fluid supply subsystem 118 (FIG. 5) preferably includes the heat exchanger 130 having a heat exchanger base 160 and a heat exchanger top cap 162 with heating coils 164 wrapped around a projection 166. The heat exchanger 130 preferably includes a fluid inlet 168 through which fluid flows into the heat exchanger 130 and a fluid outlet 170 through which heated fluid is discharged from the heat exchanger 130. In one embodiment, prior to infusing fluid into a capsule of a knee of a leg being evaluated, the heat exchanger 130 heats the infusion fluid to a temperature that replicates the body temperature of a human. In one embodiment, the heat exchanger heats the infusion fluid to approximately 37 degrees Celsius, which is compatible for testing sutures used on human body parts.

Figure 7:
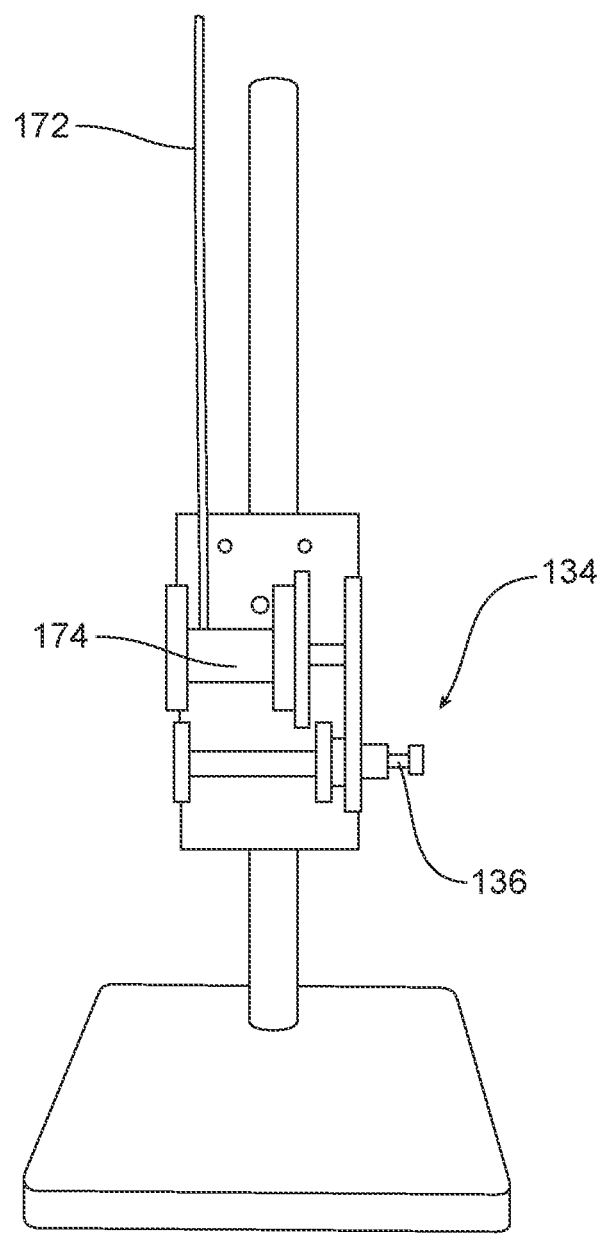
FIG. 7 is an end view of a winch that is used to raise and lower a fluid feed container of the fluid supply subsystem shown in FIG. 5, in accordance with one embodiment of the present patent application.

Referring to FIG. 7, the system 100 (FIG. 1) for testing suture performance preferably includes the winch 134 having a winch handle 136 that is utilized for raising and lowering the fluid feed container 120 (FIG. 5) that contains the infusion fluid. In one embodiment, the winch 134 preferably includes a winch cable 172 that is connected to the fluid feed container 120 (FIG. 5). The winch cable 172 is preferably configured to be wound about a spool 174, which is designed to collect the winch cable onto the spool as the spool is rotated using the winch handle 136.

Figure 8:
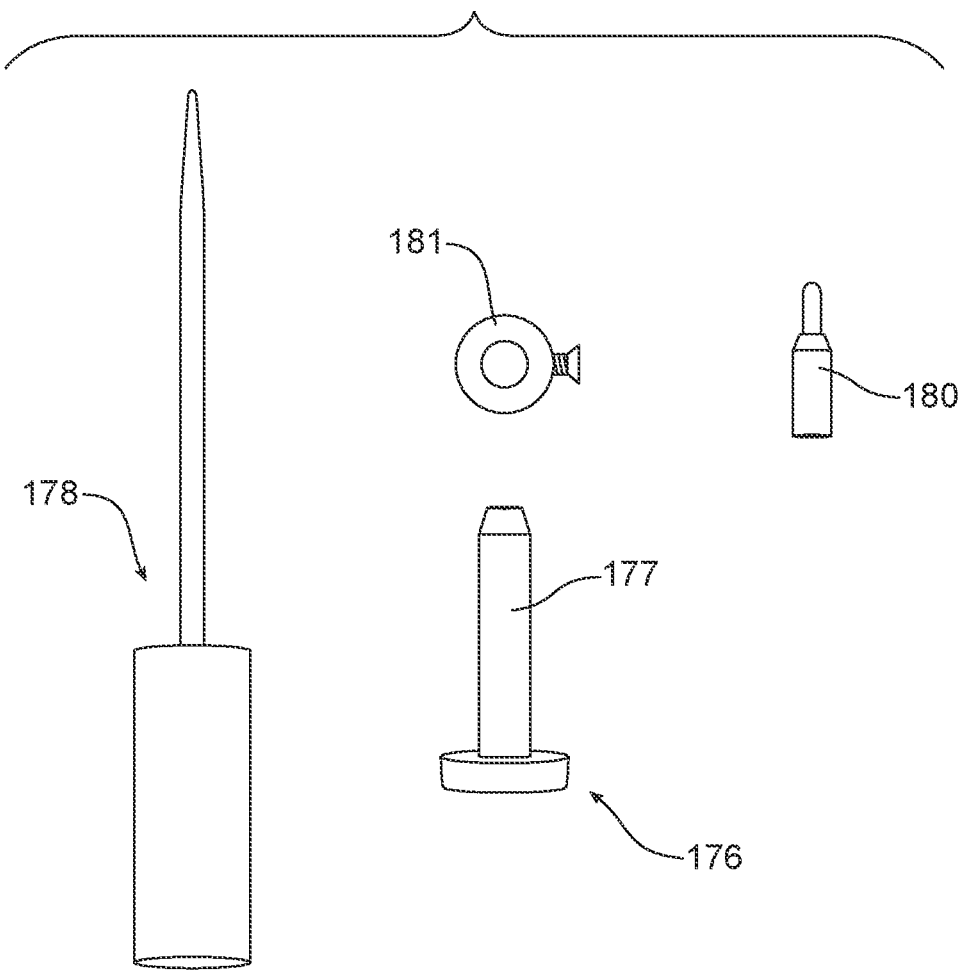
FIG. 8 is a top perspective view of an insertion tool, an infusion cannula with a retaining ring, and a circular knife, in accordance with one embodiment of the present patent application.

Referring to FIG. 8, in one embodiment, an infusion cannula 176 may be inserted into a capsule of a knee of a cadaver leg to infuse fluid inside the capsule. In one embodiment, an insertion tool 178 and a circular knife 180 may be utilized for forming a circular opening in the capsule and inserting the infusion cannula 176 into the circular opening. In one embodiment, the infusion cannula 176 may be coupled with the infusion fluid tube 138 of the system 100 (FIG. 1) for infusing fluid inside the capsule of a knee. In one embodiment, the pressure transducer 144 (FIG. 1) is preferably passed through the infusion fluid tube 138 (FIG. 1) and a central conduit of the infusion cannula 176 for monitoring the pressure of the fluid within the capsule of the knee.

Figure 9:
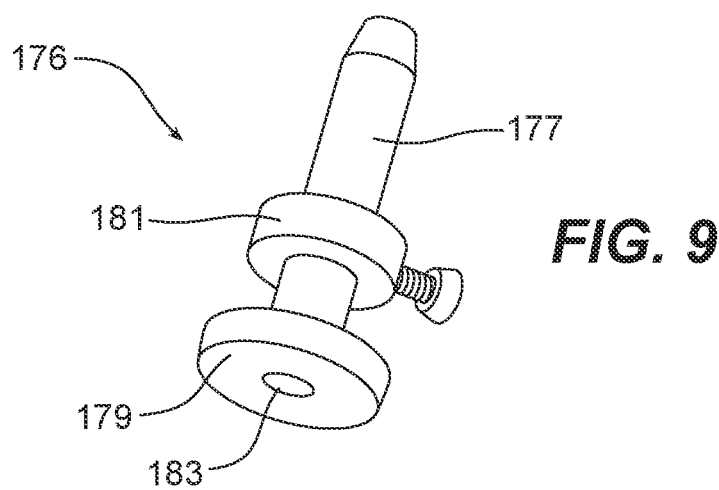
FIG. 9 is a perspective view of the infusion cannula and the retaining ring of FIG. 8, in accordance with one embodiment of the present patent application.

Referring to FIGS. 8 and 9, in one embodiment, the infusion cannula 176 may have a stem 177, a flange 179 secured to an end of the stem 177, and a retaining ring 181 that slides over the stem 177 for opposing the flange 179. The stem 177 is preferably hollow and has an elongated conduit that is aligned with an opening 183 formed at a major face of the flange 179. In one embodiment, the flange 179 may have an outer perimeter having spaced openings that provide supplemental paths for infusing fluid into a capsule of a knee.

In one embodiment, the infusion cannula 176 preferably includes a retaining ring 181 that is adapted to slide over the stem 177 for securing the infusion cannula to the knee capsule. In one embodiment, the body of the infusion cannula 176 is passed through a surgical opening and is positioned inside the knee capsule, whereupon the stem 177 of the infusion cannula is preferably passed through the circular opening formed in the capsule. At this stage, the flange 179 is located inside the capsule and the stem 177 extends to outside the capsule. The retaining ring 181 is disposed over the portion of the stem 177 that projects outside the capsule and is locked in place along the length of the stem. With the retaining ring secured in place, the capsule tissue is preferably compressed between the retaining ring 181 and the flange 179. A set screw may be tightened for securing the retaining ring to the stem.

Figure 10:
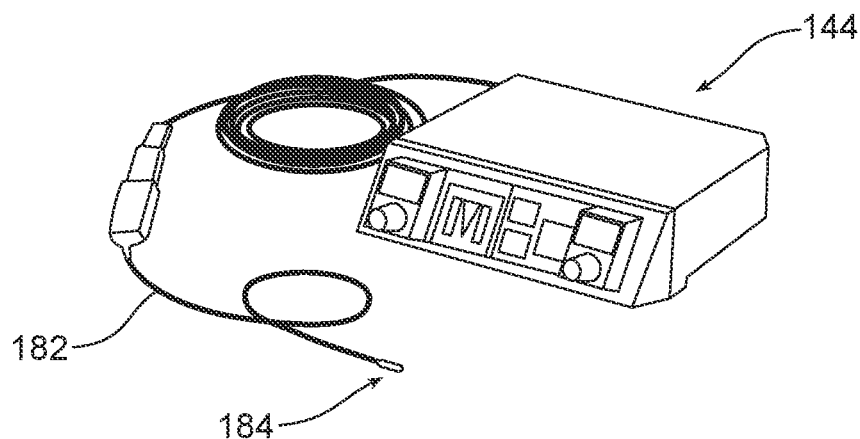
FIG. 10 is a perspective view of a pressure monitoring subsystem including a pressure monitoring catheter, in accordance with one embodiment of the present patent application.

Referring to FIG. 10, in one embodiment, the pressure monitoring subsystem 144 desirably monitors the pressure of the fluid that is infused into the capsule of the knee. In one embodiment, the pressure monitoring subsystem desirably includes a flexible, elongated pressure monitoring catheter 182 having a distal end 184 with a pressure sensor that is disposed inside the capsule of the knee for monitoring the pressure level of the fluid within the capsule.

Figure 11:
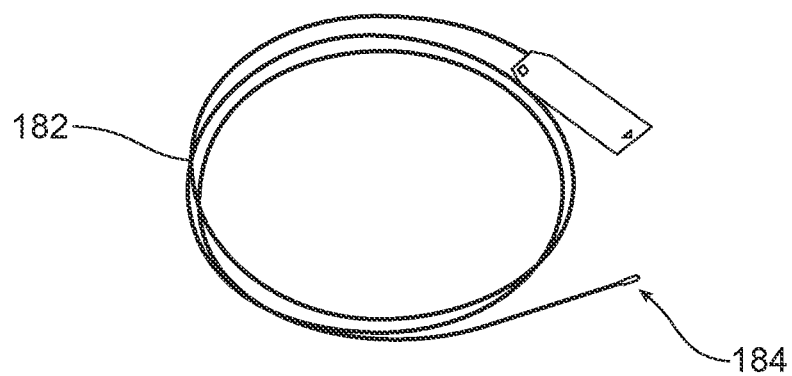
FIG. 11 is a top perspective view of the pressure monitoring catheter shown in FIG. 10.

FIG. 11 shows the pressure monitoring catheter 182 having the distal end 184 that is adapted for being disposed within a knee capsule for monitoring the fluid pressure inside the capsule during testing and evaluation of sutures. The pressure monitoring catheter is preferably flexible.

Figure 12:
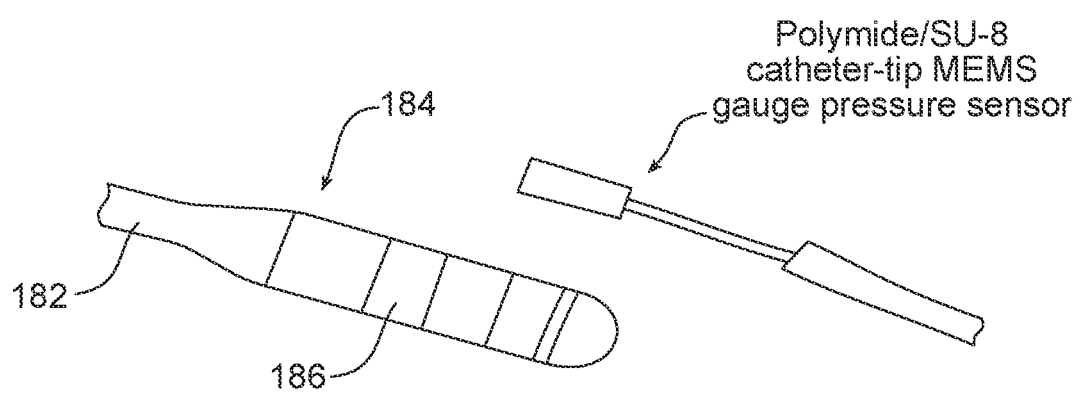
FIG. 12 shows a pressure sensor located at the distal end of the pressure monitoring catheter of FIG. 11, in accordance with one embodiment of the present patent application.

Referring to FIG. 12, in one embodiment, a pressure sensor 186 is preferably located at the distal end 184 of the flexible conduit 182 (FIG. 11). The pressure sensor 186 preferably monitors the pressure readings for the fluid infused into the capsule and transmits the information to the system controller 142 (FIG. 1) for continuously monitoring pressure levels within the capsule.

Figure 13:
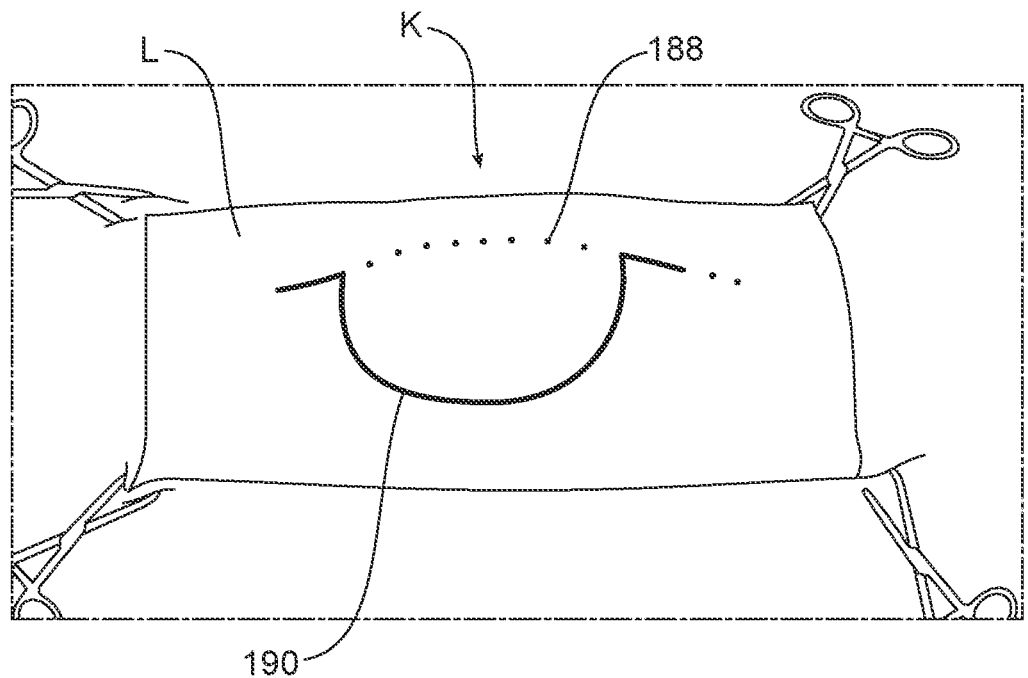
FIG. 13 shows a first step of a method of evaluating the performance of a suture, in accordance with one embodiment of the present patent application.

Referring to FIG. 13, in one embodiment, surgical openings (a/k/a wounds) are formed in a knee K of a cadaver leg L and at least one of the surgical openings is sutured so that the efficacy, strength and/or performance of the sutures may be evaluated. In FIG. 13, the knee K is prepared for surgery by marking the outer skin surface, whereby a dotted line 188 indicates a skin incision line and a solid line 190 indicates where a capsule incision will be performed on the medial side of the leg L, to one side of the capsule.

Figure 14:
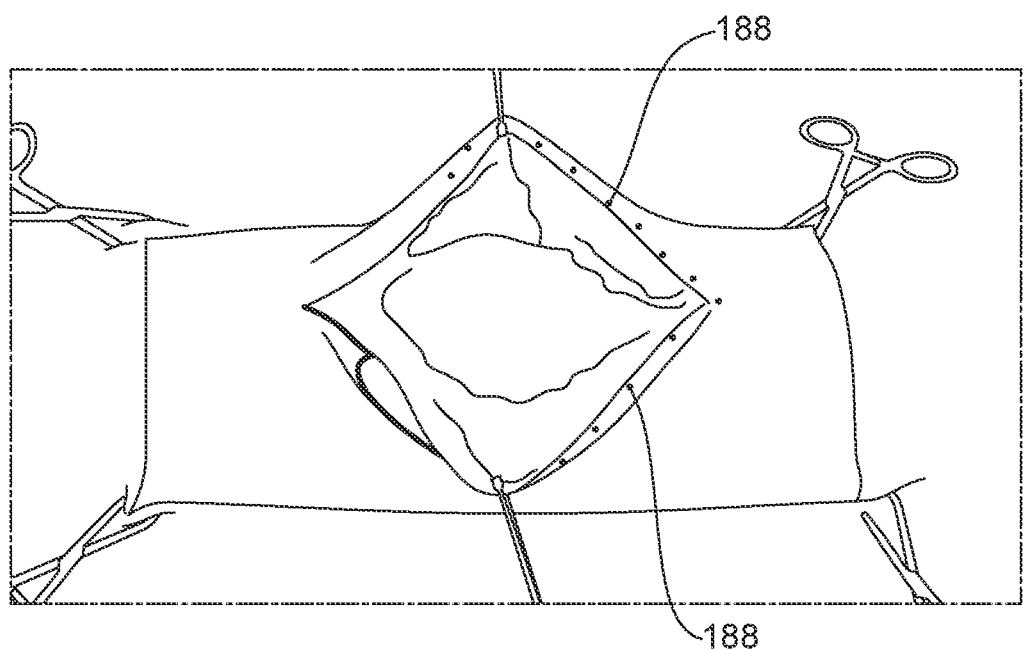
FIG. 14 shows a second step of a method of evaluating the performance of a suture, in accordance with one embodiment of the present patent application.

Referring to FIGS. 13 and 14, in one embodiment, the skin and the subcutaneous tissue are incised to approximately 2 cm cranial and caudal of the capsule. The incision is preferably made along the dotted line 188 formed on the outer surface of the skin.

Figure 15:
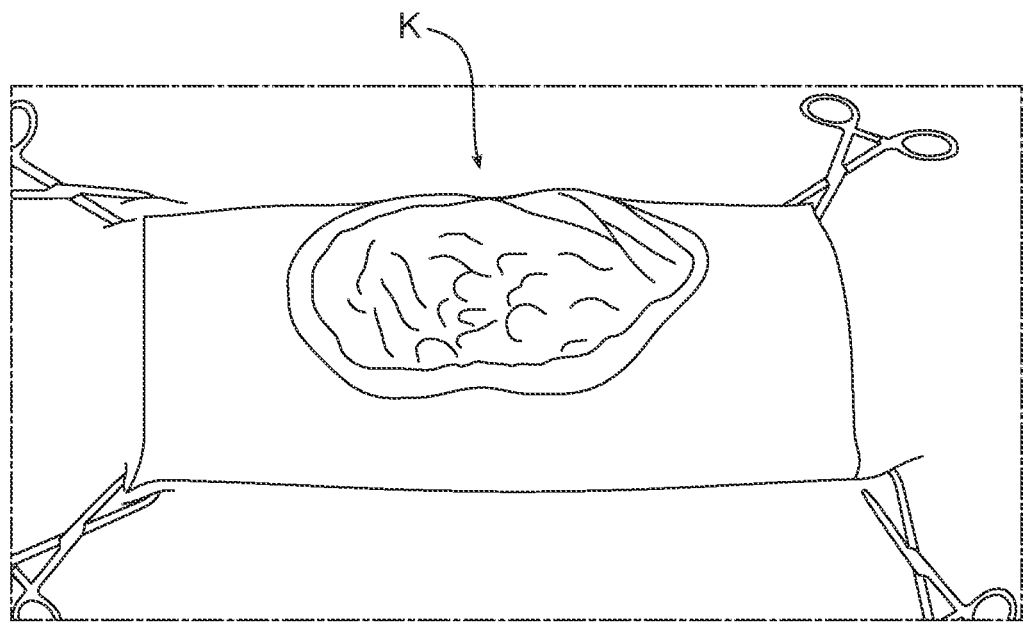
FIG. 15 shows a third step of a method of evaluating the performance of a suture, in accordance with one embodiment of the present patent application.

Referring to FIG. 15, after the skin and subcutaneous tissue have been incised along the dotted line 188 (FIG. 13), the skin and subcutaneous layer will be removed from over the knee K.

Figure 16:
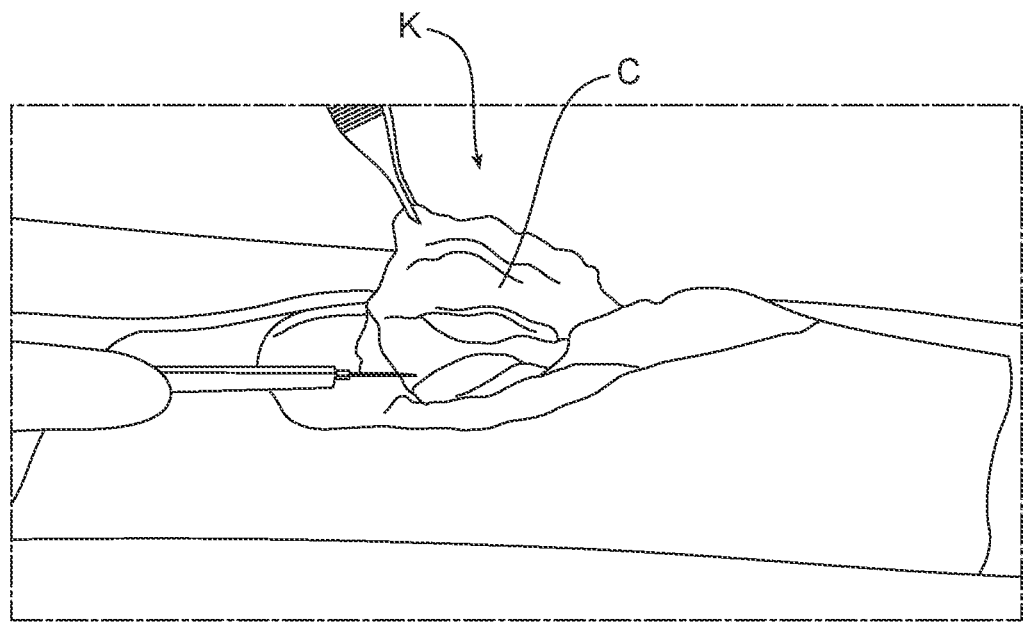
FIG. 16 shows a fourth step of a method of evaluating the performance of a suture, in accordance with one embodiment of the present patent application.

Referring to FIG. 16, in one embodiment, the knee capsule including connective tissue and the synovial membrane are incised along the medial edge of the patella. The incision is made along the solid line 190 shown and described above in FIG. 13. The incision shown in FIG. 16 opens the knee capsule C of the knee K. The knee capsule C may be flushed with fluids such as distilled water via a bulb syringe followed by suction to remove any residual synovial fluid.

Figure 17:
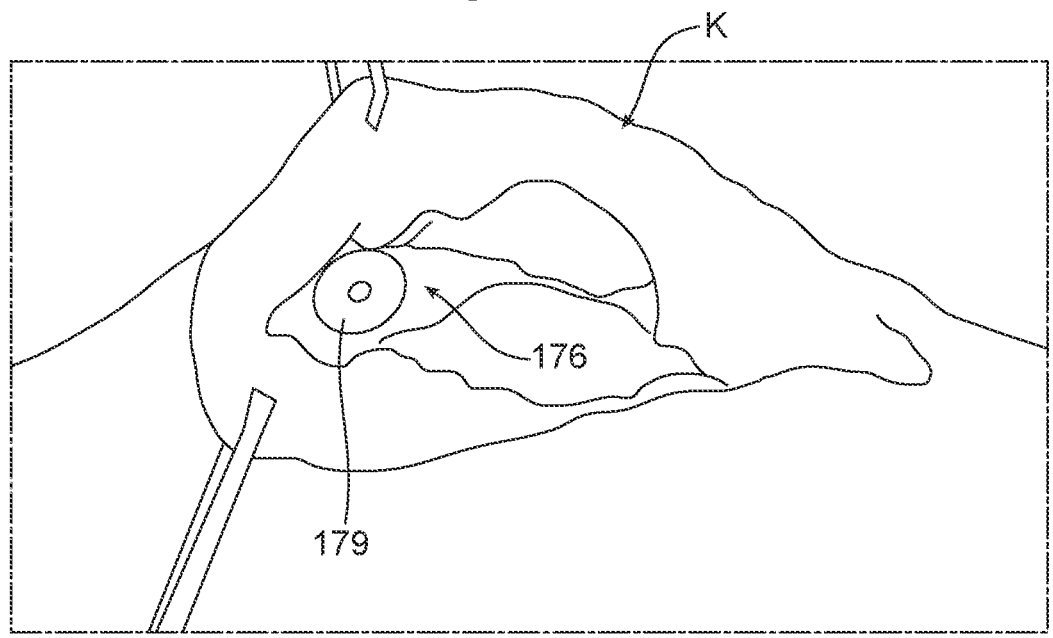
FIG. 17 shows a fifth step of a method of evaluating the performance of a suture, in accordance with one embodiment of the present patent application.

Referring to FIG. 17, in one embodiment, the infusion cannula 176 (FIG. 9) and a pressure sensor 186 (FIG. 12) are desirably inserted into the intracapsular cavity of the suprapatellar pouch of the knee K using the insertion tool 178 and the circular knife 180 (FIG. 8) to create a circular hole or opening in the knee capsule. FIG. 17 shows the infusion cannula 176 after placement inside the knee capsule with the flange 179 pressed against the inside wall of the knee capsule. The infusion cannula 176 is desirably placed from inside out and may be anchored to the capsule using the retaining ring 181 (FIG. 9) that is preferably locked over the elongated stem 177 (FIG. 9) of the infusion cannula 176. The infusion cannula may also be secured to the outer surface of the capsule using a securing element such as a purse string suture. In one embodiment, an adhesive material such as the adhesive material sold by Johnson & Johnson Corporation of New Brunswick, N.J. under the trademark DERMABOND® may be utilized to repair any leaks that are may be present around the infusion cannula 176.

Figure 18A:
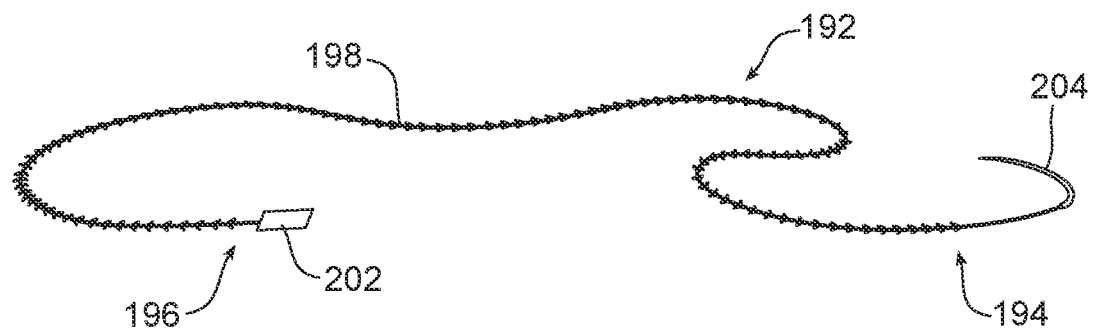
FIG. 18A is a perspective view of a barbed suture having a suture needle secured to a first end of the barbed suture and a stop secured to a second end of the barbed suture, in accordance with one embodiment of the present patent application.
Figure 18B:
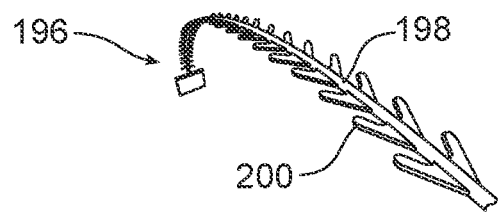
FIG. 18B is a magnified view of a section of the barbed suture shown in FIG. 18A.

Referring to FIGS. 18A and 18B, in one embodiment, a suture 192 may be utilized for closing the surgical opening that was formed in the capsule (see FIG. 16). The suture 192 preferably has a leading end 194 and a trailing end 196. The suture 192 preferably includes barbs 198 that project outwardly from an elongated filamentary element 200. The suture 192 preferably includes a stop 202 secured to the trailing end 196 of the barbed suture 192. A suture needle 204, such as a C-1 suture needle, is preferably secured to the leading end 194 of the barbed suture 192. In one embodiment, the barbed suture 192 may be a barbed suture sold by Johnson & Johnson Corporation of New Brunswick, N.J. under the trademark STRATAFIX® and the suture needle 204 may be a CT-1 needle. In one embodiment, a template may be utilized to mark the site of each needle penetration to standardize the suture placement between leg specimens. In one embodiment, the bites will be approximately 8 mm apart and 6 mm from the incision edge that defines the surgical opening. In one embodiment, sutures are used to close the incision edge with the knee flexed at approximately 30 degrees.

In one embodiment, the barbed suture 192 is utilized so that the edge of the tissue will be everted during needle passage to insure a full wall thickness passage of the suture needle 204 with the synovial membrane captured during each pass of the suture needle. In one embodiment, before closure of the last few centimeters of the surgical opening (e.g., the arthrotomy), water (e.g., warm distilled water) may be flushed through the infusion cannula to de-air the capsule of any residual air.

Figure 19:
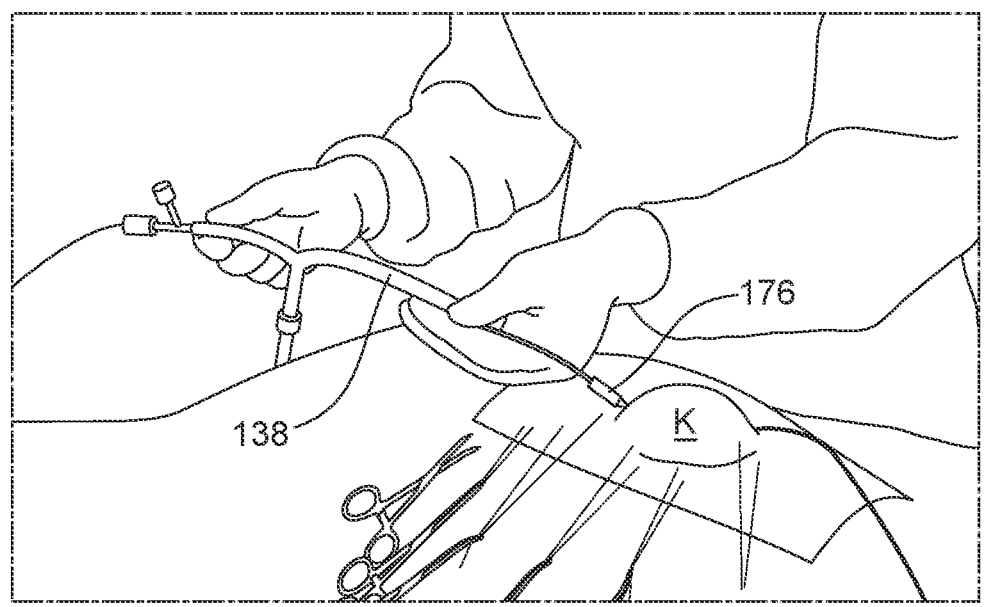
FIG. 19 shows a step of a method of coupling an infusion fluid tube to an infusion cannula for infusing fluid into a capsule of a knee, in accordance with one embodiment of the present patent application.

Referring to FIG. 19, after the knee capsule has been sutured to close the surgical opening, with the infusion cannula 176 inserted into the capsule, the infusion fluid tube 138 (FIG. 1) is preferably coupled with the stem of the infusion cannula 176 that projects out of the capsule of the knee K.

Figure 20:
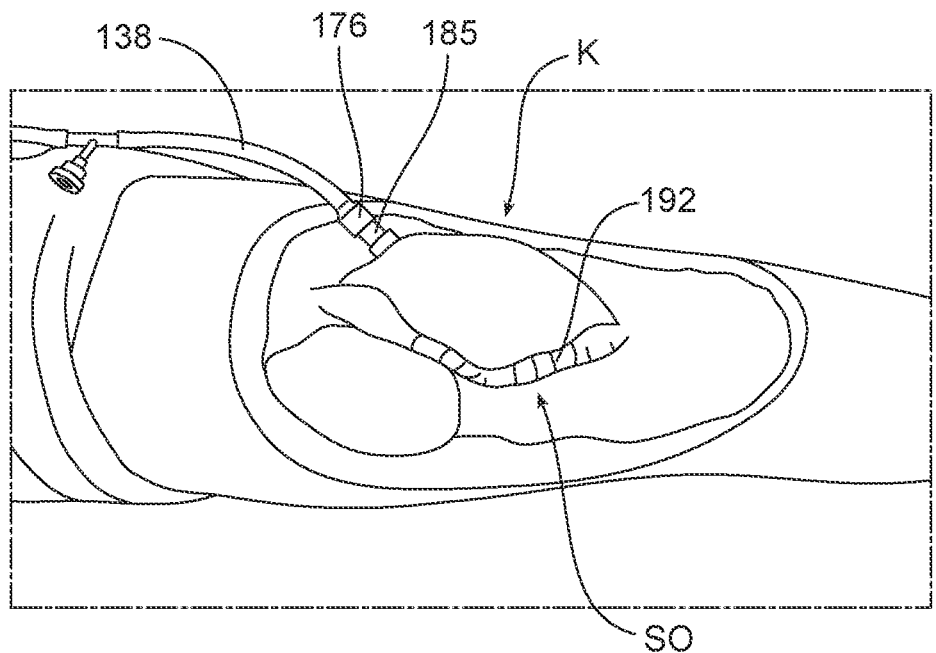
FIG. 20 shows a top view of a knee having an infusion cannula passing through a capsule of the knee and an infusion fluid tube coupled with the infusion cannula, in accordance with one embodiment of the present patent application.

FIG. 20 shows the surgical opening SO after the suture 192 has been utilized to close the surgical opening formed in the knee capsule. The infusion cannula 176 extends through an opening formed in the capsule and may be held in place utilizing a purse string suture 185. The infusion fluid tube 138 is coupled with the infusion cannula 176 to supply infusing fluid to the inside of the capsule of the knee K. The pressure monitoring catheter 182 and the pressure sensor 186 (FIGS. 11 and 12) preferably pass through the infusion fluid tube 138 and the infusion cannula 176 so that the pressure sensor is located inside the capsule of the knee K to monitor the pressure of the fluid infused into the capsule.

Figure 21:
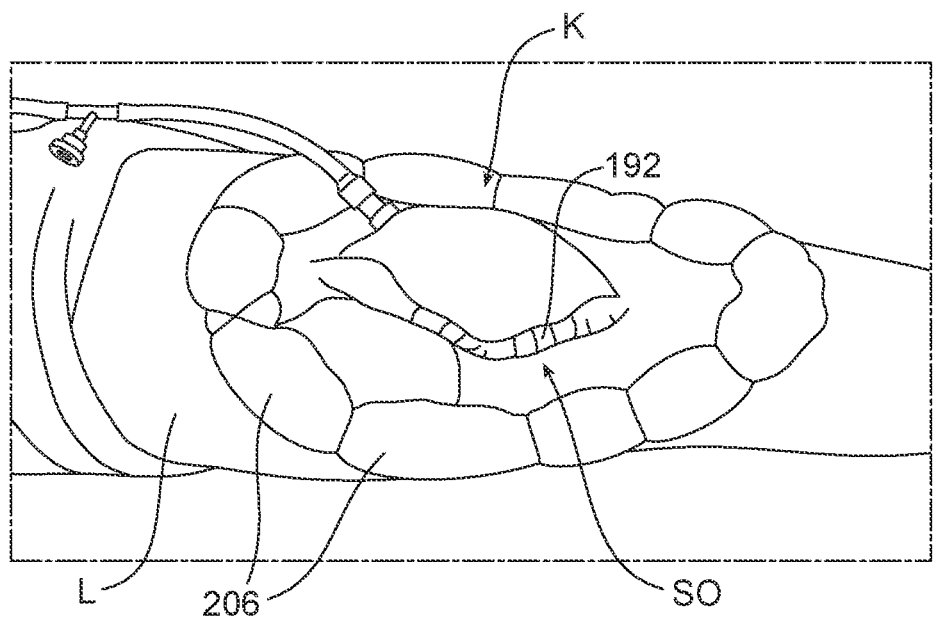
FIG. 21 shows the knee of FIG. 20 with absorbent towels secured around the perimeter of a surgical opening to collect weeping fluid, in accordance with one embodiment of the present patent application.

Referring to FIG. 21, in one embodiment, laparotomy pads 206 may be secured to the outer skin surface of the cadaver leg L prior to evaluating the performance of the suture 192. The laparotomy pads 206 desirably absorb any fluid that weeps from the subcutaneous fat and skin incisions.

Figure 22:
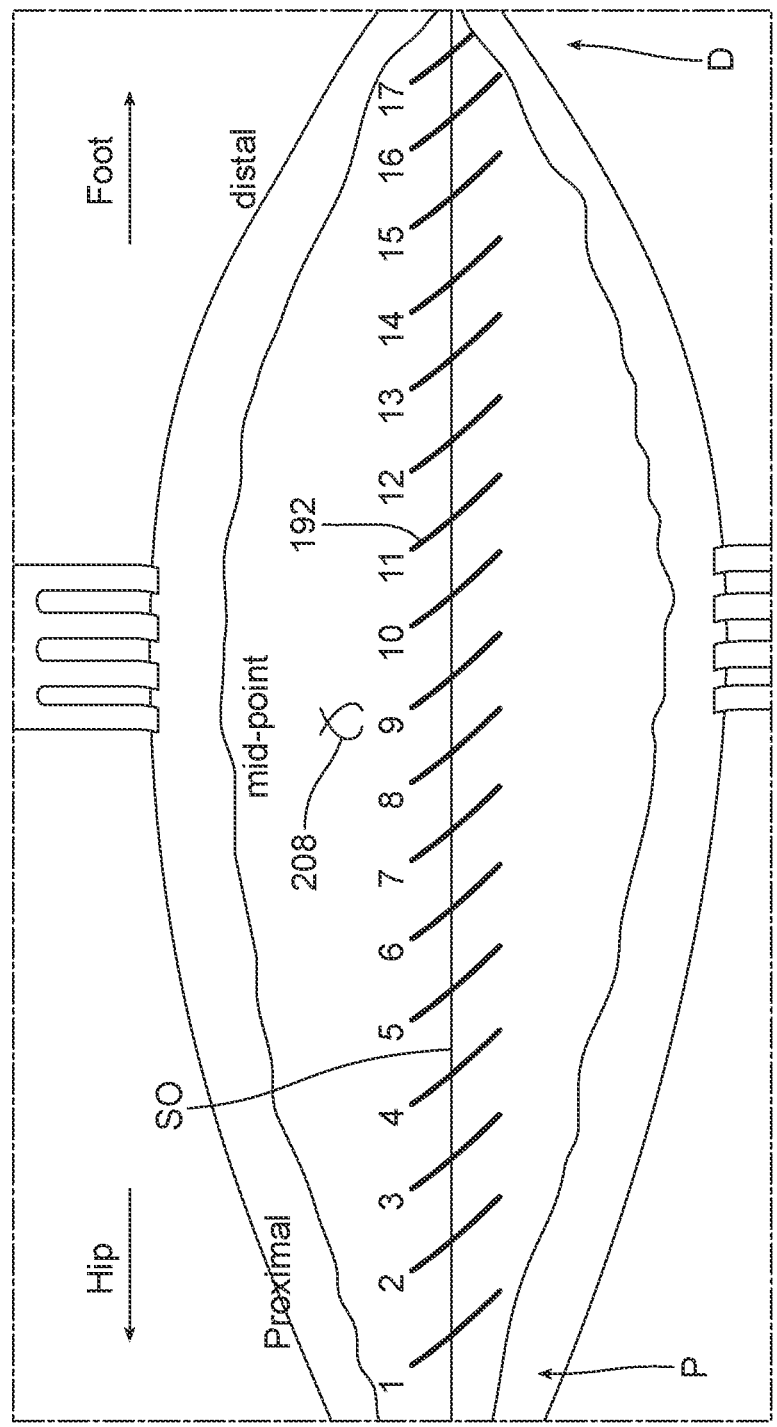
FIG. 22 shows a schematic view of a knee having a surgical opening closed by sutures with a midpoint of the sutures being designated by a marker suture, in accordance with one embodiment of the present patent application.

Referring to FIG. 22, in one embodiment, the suture 192 that is utilized to close a surgical opening SO preferably has a proximal end P that is closer to the hip of a cadaver leg and a distal end D that is closer to the foot of the cadaver leg L. In one embodiment, a marker suture 208 may be utilized for designating a midpoint of the suture 192 used to close the surgical opening SO. As will be described in more detail herein, during a step of a method of testing suture performance, a strand of the suture near the marker suture 208, such as a suture strand designated by the number 9 in FIG.

22, may be cut for evaluating the performance of the remaining sutures after the suture designated number 9 has been cut.

Figure 23:
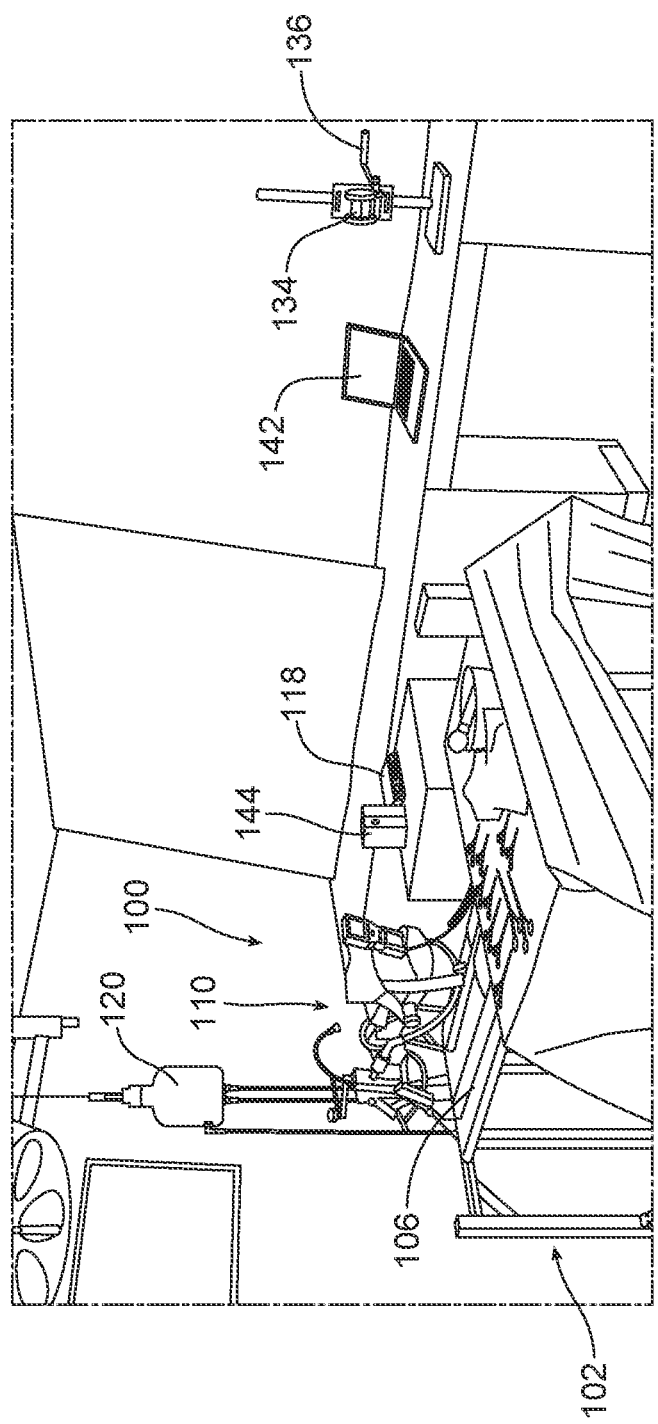
FIG. 23 shows a perspective view of a system for testing suture performance, in accordance with one embodiment of the present patent application.

Referring to FIG. 23, in one embodiment, the system 100 for evaluating the performance of a suture preferably includes the test bench 102 and the rotatable table 106 that supports the CPM machine 110. The rotatable table 106 is selectively rotatable between an upright position in which the CPM machine 110 is located above the table 106 and an inverted position in which the CPM machine 110 is upside down and located below the table 106. The collection of the fluid that leaks through the suture line is preferably accomplished when the table 106 and the CPM machine 110 are inverted. The testing system 100 preferably includes the system controller 142 that monitors and controls the fluid supply subsystem 118, the operation of the CPM machine 110, and the pressure monitoring subsystem 144 that monitors the pressure levels inside the knee capsule. The fluid supply subsystem 118 desirably includes the fluid feed container 120 that contains an infusing fluid that is infused into a capsule of a knee. Infusing fluid into the capsule of a knee enables the system to evaluate the efficacy, strength and/or performance of sutures that have been used to close a surgical opening formed in the capsule.

In one embodiment, the system 100 desirably includes a winch 134 having a winch handle 136 that may be utilized for raising and lowering the fluid feed container 120 to adjust the pressure level of the fluid infused into the knee capsule of a leg.

Figure 24:
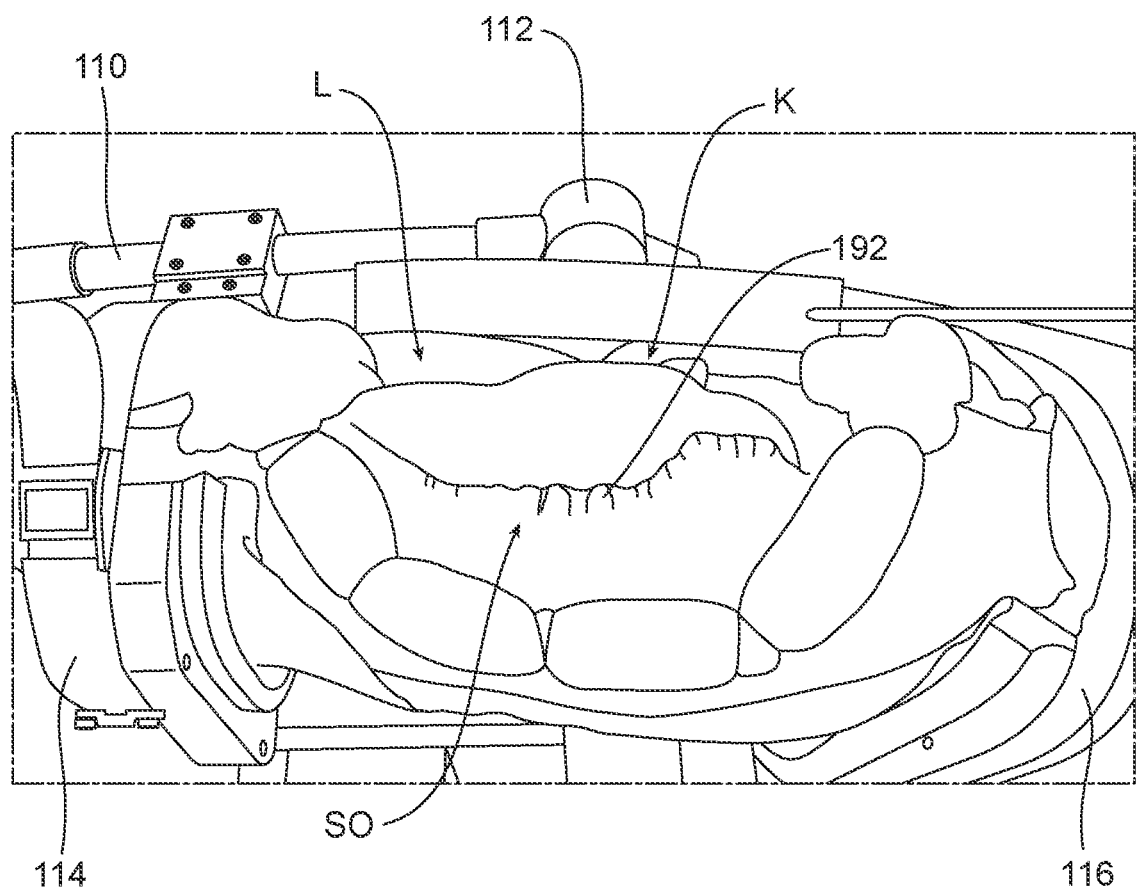
FIG. 24 is a side view of a cadaver leg secured to a CPM machine for evaluating the performance of sutures used to close a surgical opening formed in a capsule of a knee, in accordance with one embodiment of the present patent application.

Referring to FIG. 24, in one embodiment, in order to test suture performance, a cadaver leg L having a surgical opening SO closed by sutures 192 is preferably positioned onto a CPM machine 110. The knee K is preferably aligned with the articulating joint 112 of the CPM machine 110. The first leg clamp 114 is secured over the upper leg region of the leg L and the second leg clamp 116 is secured over the lower leg region of the leg L for securing the leg in place on the CPM machine 110. In one embodiment, before the leg L is secured to the CPM machine 110, the leg L is preferably wrapped in a surgical drape.

Figure 25:
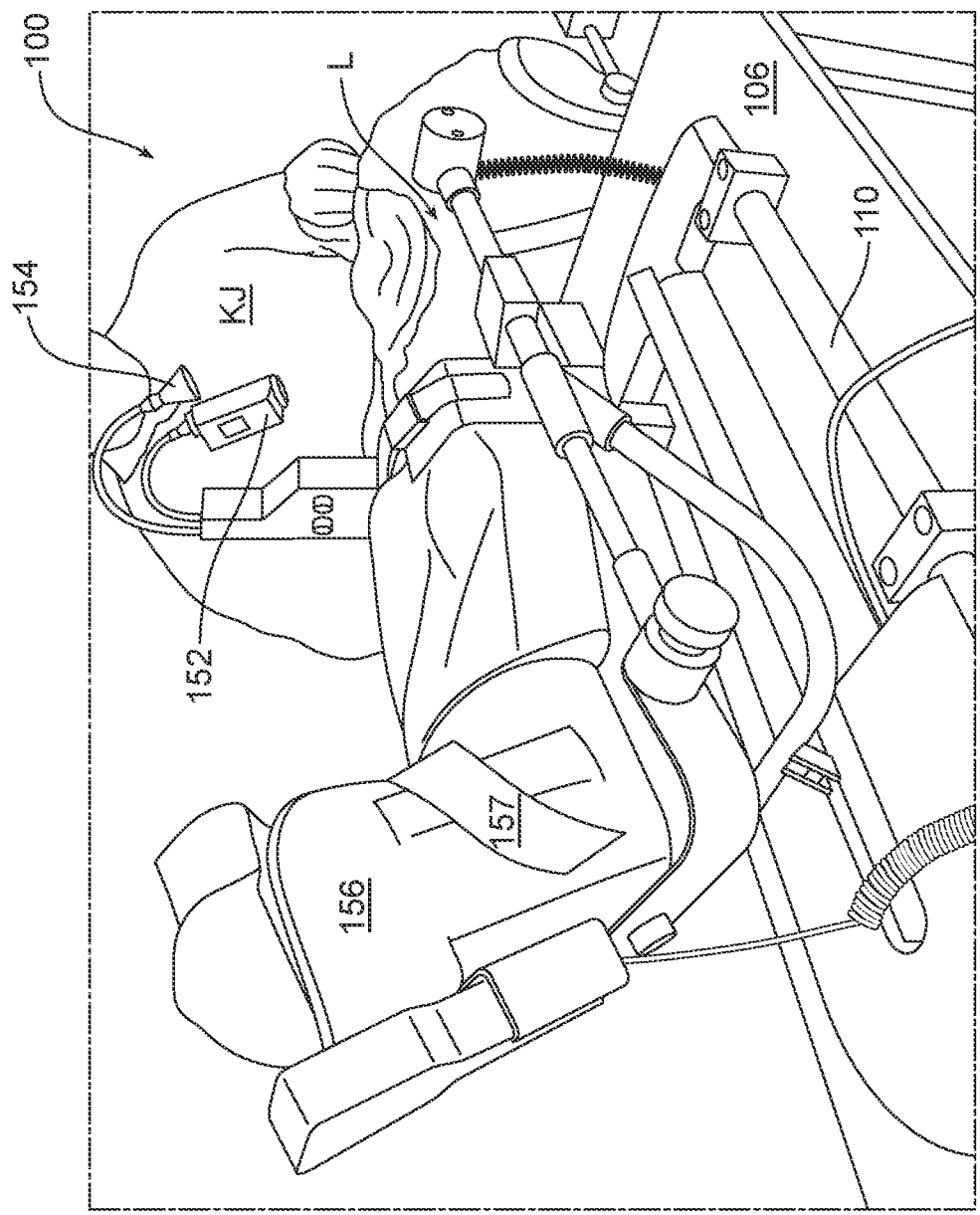
FIG. 25 shows a perspective view of the CPM machine and the cadaver leg of FIG. 24 mounted onto a rotatable table of a system for testing suture performance, in accordance with one embodiment of the present patent application.

Referring to FIG. 25, in one embodiment, the cadaver leg L, wrapped in the surgical drape, is desirably positioned on the CPM machine 110. The foot at the lower end of the leg is positioned within the foot support 156 and held in place utilizing the securing strap 157 (e.g., a securing strap having hook and loop fasteners). The camera 152 and the illuminating element 154 are directed at the knee K of the leg for monitoring the suture line during testing.

In one embodiment, at the start of a testing protocol, the rotatable table 106 of the system 100 is in an upright position so that the CPM machine 110 is located above the table 106 and extends away from the floor.

Figure 26A:
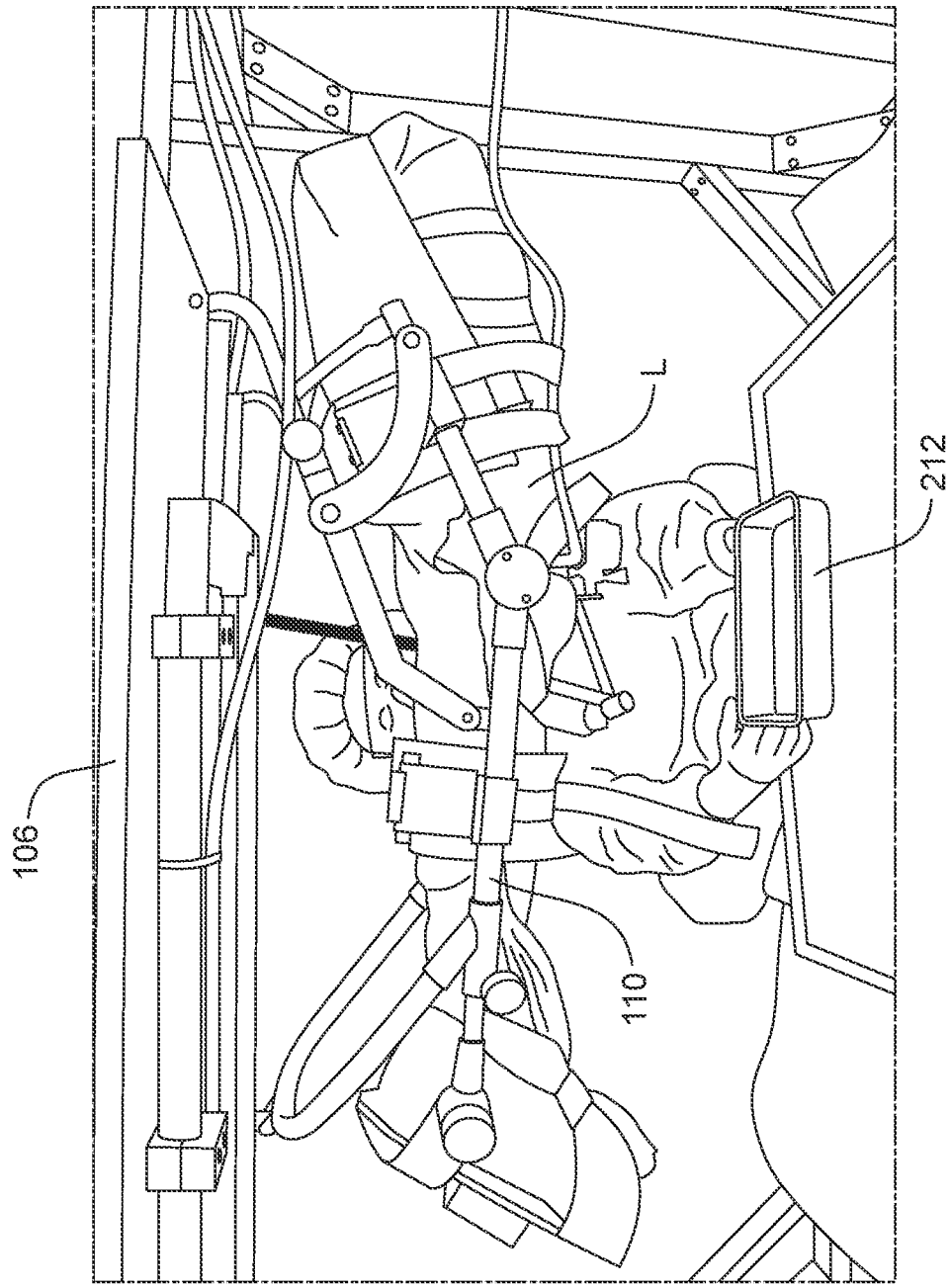
FIG. 26A shows the rotatable table and the CPM machine of FIG. 25 after the rotatable table has been inverted so that the CPM machine is located below the rotatable table, in accordance with one embodiment of the present patent application.
Figure 26B:
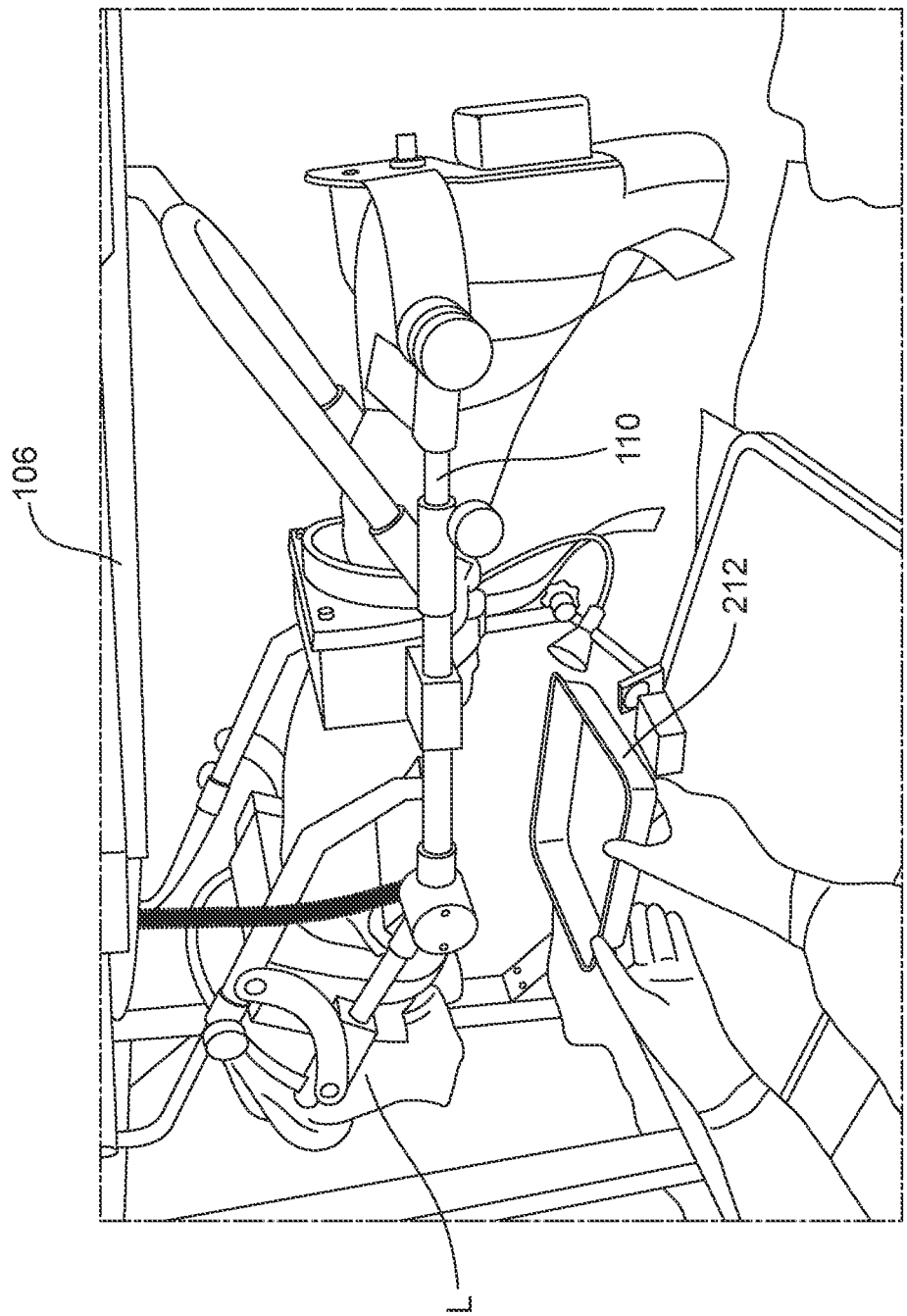
FIG. 26B shows another view of the rotatable table and the CPM machine of FIG. 26A after the rotatable table has been inverted, in accordance with one embodiment of the present patent application.

Referring to FIGS. 26A and 26B, in one embodiment, the table 106 is inverted so that the CPM machine 110 and the leg L secured to the CPM machine 110 are below the table 106. In this configuration, the CPM machine 110 and the leg L are upside down relative to the upright position shown in FIG. 25.

During testing, in order to evaluate the performance of a suture used to close a surgical opening, a fluid collection tray 212 may be used to collect fluid that seeps through the suture line that closes the surgical opening. The volume and weight of the fluid collected in the tray 212 is monitored to determine the efficacy, strength and/or performance of the suture that has been used to close the surgical opening.

Figure 27:
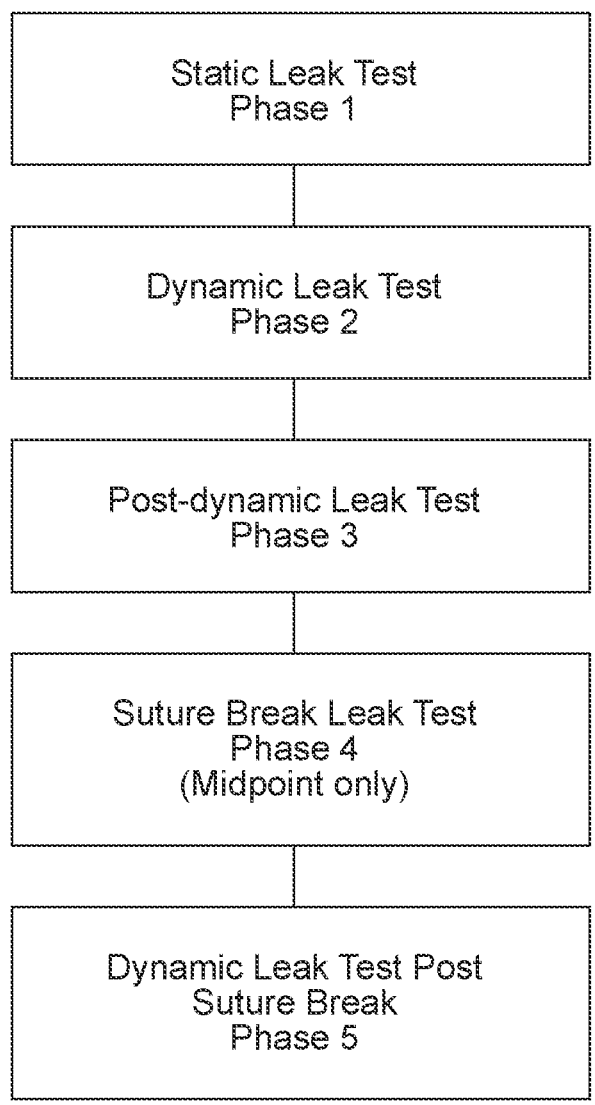
FIG. 27 is a flow chart depicting different phases of a testing protocol used for testing suture performance, in accordance with one embodiment of the present patent application.

Referring to FIG. 27, in one embodiment, a testing protocol may be utilized to evaluate the efficacy, strength and/or performance of sutures used to close surgical openings formed in knees. The sutures that are evaluated may be sutures without barbs or barbed sutures.

In one embodiment, a testing protocol is used to perform leak testing under static and dynamic conditions for intact suture lines and under simulated conditions of suture breakage through suture release testing. In one embodiment, the testing protocol assesses aquastasis through at least five phases, measuring the leak rate in each phase, in a human cadaver knee arthroplasty model. In one embodiment, a testing protocol may use only one of the phases set forth herein. The purpose and clinical relevance of each phase of the testing protocol is summarized below.

Phase 1—Pre-Dynamic Static Leak Test.

Phase 1 of the testing protocol simulates the physiological patient condition immediately following surgery when fluid accumulation occurs within the capsule and may result in increased intracapsular pressure levels of up to approximately 80 mmHg. In one embodiment, a maximum intracapsular pressure of 80 mmHg is used because tissue perfusion and bleeding will cease in the arthrotomy when the intra-compartmental pressure is 10-30 mmHg less than the minimum diastolic blood pressure. Thus, using 80 mmHg as a normotensive diastolic pressure, the upper limit of a static testing phase would desirably be 80 mmHg.

In one embodiment, one or more of the following steps may be performed during Phase 1—Pre-dynamic static leak testing: 1. After the cadaver leg is secured to the CPM machine, the table is rotated to invert the leg. 2. The fluid level in the fluid feed container is below the level of the infusion cannula that is inserted into the capsule of the knee. If the fluid feed container is above the level of the infusion cannula, the fluid feed container must be lowered. 3. A tubing clamp is removed from the infusion fluid tube to commence the flow of infusing fluid and the data acquisition system is started to measure the intracapsular pressure. 4. A fluid collection container is tared on a scale. As used herein, tared means a deduction from the gross weight of a substance and its container made in allowance for the weight of the container. 5. The fluid feed container is slowly raised using the hand winch and the capsule of the knee is infused with water at 37 degrees Celsius to a constant pressure of approximately 30 mmHg. 6. The fluid collection tray is positioned under the suture line of the knee and the fluid is collected for three (3) minutes. The fluid collection tray is preferably weighed at the end of the three (3) minute collection period and the weight of the fluid recorded in data sheets. 7. If the suture line leak rate is less than one (1) mL per minute (leak rate<1 mL/minute), the leg is accepted into the study. 8. If the suture line leak rate is greater than or equal to one (1) mL per minute (leak rate 1 mL per minute), the knee closure will be considered a technical error and the surgeon will have the option of repairing the leak or discarding the cadaver leg from the study. 9. If the decision is to repair the leg, the leg secured to the CPM machine will be rotated upright, and the leak may be repaired with sutures. 10. After the repair, the leg secured to the CPM machine is again inverted and checked for leaks at 30 mmHg for three (3) minutes. Steps 8-10 are repeated until no leaks are found. 11. If the knee cannot be repaired, it will be excluded from analysis. 12. Upon acceptance of the specimen, the fluid feed container will be raised until the intracapsular pressure measurement is increased by 10 mmHg to approximately 40 mmHg. 13. A fluid collection container (e.g., a tray) will be tared on a scale. 14. The fluid collection container is positioned under the suture line of the knee and the fluid collected for three (3) minutes. After three minutes, the fluid collection container will be weighed and the weight of the fluid recorded in the data sheets. 15. Steps 12-14 are repeated, raising the intracapsular pressure approximately 10 mmHg per leak assessment up to 80 mmHg. If any knee sustains a critical leak (defined as an inability for the infusion pump to maintain a constant pressure), testing will be discontinued for the knee, and the cadaver leg will be considered a failure for all further testing points.

Phase 2—Dynamic Motion Leak Test.

Phase 2 of the testing protocol simulates the patient condition during post-operative physical therapy when the knee is cycled through a range of motion from 0 to 120 degrees using a continuous passive motion (CPM) machine. The intracapsular fluid pressure changes throughout the extending and flexing cycle of the knee due to changes in the volume of the capsule, creating pressure levels that far exceed the 80 mmHg level that was present during the static test (e.g., 400-500 mmHg peak pressure) leading to potentially higher leak rates and possibly permanent change in the tissue or stretching of the suture.

In one embodiment, one or more of the following steps may be performed during Phase 2—Dynamic motion leak test: 1. The cadaver knee will undergo 20 range of motion (ROM) cycles at a rate of approximately 100 seconds per cycle with the use of the CPM machine. As used herein, one ROM cycle is defined as the knee going from 0 degrees of extension to 120 degrees of flexion and returning to 0 degrees of extension. 2. As the knee is undergoing the 20 ROM cycles, the leak volume will be measured. 3. A fluid collection container will be tared on a scale. 4. The fluid collection container is positioned under the suture line of the knee and the fluid collected for the entire $5^{th}$ ROM cycle. 5. The fluid collection container is weighed at the end of the $5^{th}$ ROM cycle and the weight of the fluid recorded in the data sheets. 6. Steps 2-5 are repeated for the $10^{th}$, $15^{th}$, and $20^{th}$ ROM cycles. In one embodiment, if a knee sustains a critical leak (defined as an inability for the pressure pump to maintain a constant pressure), testing will be discontinued for the cadaver knee that suffered the critical leak, and the cadaver leg will be considered a failure and removed from all further testing.

Phase 3—Post Dynamic Static Leak Test.

Phase 3 of the testing protocol simulates the patient condition following physical therapy and assesses if any permanent physical change occurred to the suture seal of the capsule during the dynamic motion phase (i.e., Phase 2) through a comparison of a first static leak test that precedes the dynamic motion phase and a second static leak test that follows the dynamic motion phase.

In one embodiment, one or more of the following steps may be performed during Phase 3—Post-dynamic static leak testing: 1. The leg is positioned at 30 degrees flexion. 2. The leg is infused with water (e.g., distilled water) having a temperature of 37 degrees Celsius and a constant pressure of 30 mmHg. 3. The height of the fluid feed container is adjusted until a proper pressure reading (e.g., 30 mmHg) is obtained. 4. A fluid collection container is tared on a scale. 5. The fluid collection container is positioned under the suture line of the knee and the fluid collected for three (3) minutes. 6. The fluid collection container is weighed at the end of the three (3) minute collection period and the weight of the fluid recorded in the data sheets. 7. Steps 4-6 are repeated, raising the intracapsular pressure approximately 10 mmHg per leak assessment up to 80 mmHg.

Phase 4—Suture Release Static Leak Test.

Phase 4 of the testing protocol simulates the condition of a suture breaking at a midpoint of the surgical opening closure during post-operative recovery. Phase 4 of testing simulates the condition for patients that have gone through the dynamic motion phase of physical therapy. The leak rate of the surgical opening closure following one or more suture releases (breakage) may be significantly different between non-barbed and barbed sutures.

After completion of the Post-Dynamic static leak testing of Phase 3, the knee will undergo suture release while the intracapsular pressure is maintained at 80 mmHg. In one embodiment, a midpoint suture loop is cut as the knee is held in 30 degrees of flexion and the fluid leakage will be collected over a three minute time period. For a suture line having even numbered loops, the loop to be cut is the loop immediately distal to the midpoint. In one embodiment, one or more of the following steps may be performed during Phase 4—Suture Release Leak Testing: 1. A fluid collection container will be tared on a scale. 2. The midpoint suture loop is cut with the knee in 30 degrees flexion. 3. The height of the fluid reservoir is adjusted until 80 mmHg is achieved. If it is not possible to achieve an intracapsular pressure of 80 mmHg, the specimen will be recorded as having reached a critical leak and no further testing will be performed. As used herein, the terminology "critical leakage" is defined as the inability to maintain an intracapsular pressure of 80 mmHg. 4. The fluid collection container is positioned under the suture line of the knee and the fluid collected for three minutes. 5. The fluid collection container is weighed at the end of the three minute collection period and the weight of the fluid recorded in the data sheets.

Phase 5—Post Suture Break Dynamic Motion Leak Test.

Phase 5 of the testing protocol simulates the condition following a suture break as the knee undergoes a full range of motion. The leak rate will be assessed during five full ROM cycles on the CPM machine.

After the completion of the suture release leak testing of Phase 4, the knee will be set to 30 degrees flexion and the intracapsular pressure will be adjusted to 80 mmHg. The knee will undergo dynamic motion, with each cycle starting from 30 degrees flexion, extending to 0 degrees, moving to a maximum flexion at 120 degrees, and returning to 30 degrees on the CPM machine.

In one embodiment, one or more of the following steps may be performed during Phase 5—Post suture break dynamic motion leak test: 1. A fluid collection container is tared on a scale. 2. The fluid collection container is positioned under the suture line of the knee and the fluid collected for each cycle as described above. 3. The fluid collection container is weighed at the end of the cycle, and the weight of the fluid recorded in the data sheets. 4. Steps 2-3 are repeated for five (5) consecutive cycles without stopping the motion or re-adjusting the intracapsular pressure.

Post Testing Suture Inspection. In one embodiment, after completing Phases 1-5 of the testing protocol as outlined above, the suture line is cut open to inspect each suture pass through the tissue. The suture pass should preferably be of a full wall thickness, capturing the synovial membrane and all layers of tissue. If inspection indicates that any suture pass was of incomplete thickness, the number of incomplete thickness passes and the approximate location of the incomplete thickness passes along the incision line will be recorded in the data sheets.

Figure 28:
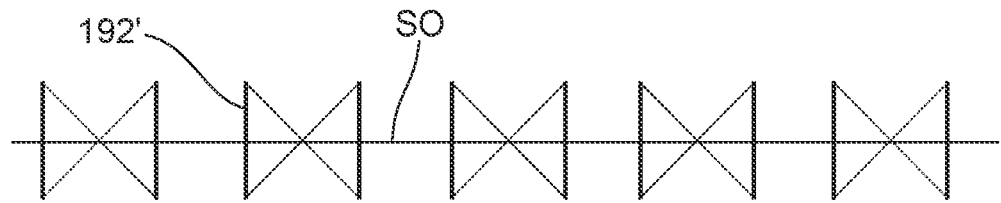
FIG. 28 shows a schematic view of a first suture pattern used with conventional sutures for closing a surgical opening, in accordance with one embodiment of the present patent application.

Referring to FIG. 28, in one embodiment, barbless sutures 192' having figure eight patterns are used for closing a surgical opening SO. The barbless sutures 192' may be similar to that sold by Johnson & Johnson Corporation of New Brunswick, N.J., under the trademark VICRYL®.

Figure 29:
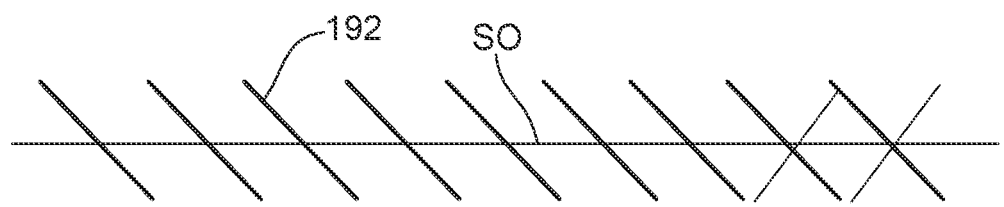
FIG. 29 shows a schematic view of a second suture pattern used with barbed sutures for closing a surgical opening, in accordance with one embodiment of the present patent application.

Referring to FIG. 29, in one embodiment, a barbed suture 192 may be used for closing a surgical opening SO. The barbed suture 192 may be similar to that sold by Johnson & Johnson Corporation of New Brunswick, N.J., under the trademark STRATAFIX®.

Figure 30:
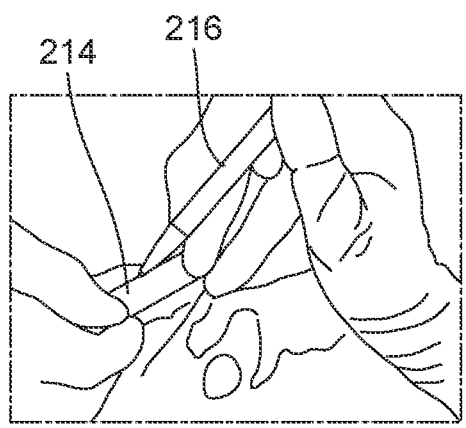
FIG. 30 is a perspective view of a method of using a template to mark sites that will be penetrated by a suture needle during a suturing operation, in accordance with one embodiment of the present patent application.
Figure 31:
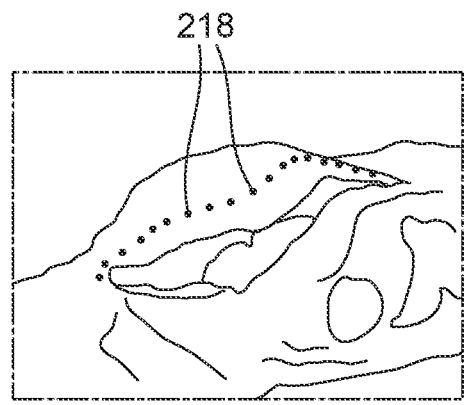
FIG. 31 is a perspective view of a capsule of a knee after the template of FIG. 30 has been used to mark the capsule with visible indicia indicating the sites that will be penetrated by the suture needle during a suturing operation, in accordance with one embodiment of the present patent application.

Referring to FIG. 30, in one embodiment, a template 214 may be used to mark the site of each needle penetration to standardize the suture placement between cadaver leg specimens. In one embodiment, the template generates visible markings that are approximately 8 mm apart and 6 mm from the incision edge of the surgical opening formed in the tissue. In one embodiment, a marker 216 may be used with the template 214 for generating the visible markings on the tissue. FIG. 31 shows the visible markings 218 formed on the tissue, whereby the visible markings are adjacent the incision line that formed the surgical opening.

Referring to FIGS. 32 and 33, in one embodiment, as part of a testing protocol to test the performance of sutures, an infusion cannula 276 having a barb 277 at a distal end of a cannula stem may be inserted into a knee capsule to infuse fluid inside the capsule. In one embodiment, an insertion tool 278 having an insertion tool shaft 279 and a circular knife 280 may be utilized for forming an opening in a knee capsule so that the infusion cannula 276 may be inserted into the knee capsule. In one embodiment, the infusion cannula 276 is preferably slid over the insertion tool shaft 279 of the insertion tool 278 and the circular knife 280 is secured over the free, distal end of the insertion tool shaft 279.

Referring to FIG. 34A, in one embodiment, with the surgical opening formed in the knee capsule still open, the insertion tool 278 is desirably maneuvered to abut a sharpened end of the circular knife 280 against the outer surface of the capsule C of the knee.

Figure 34B:
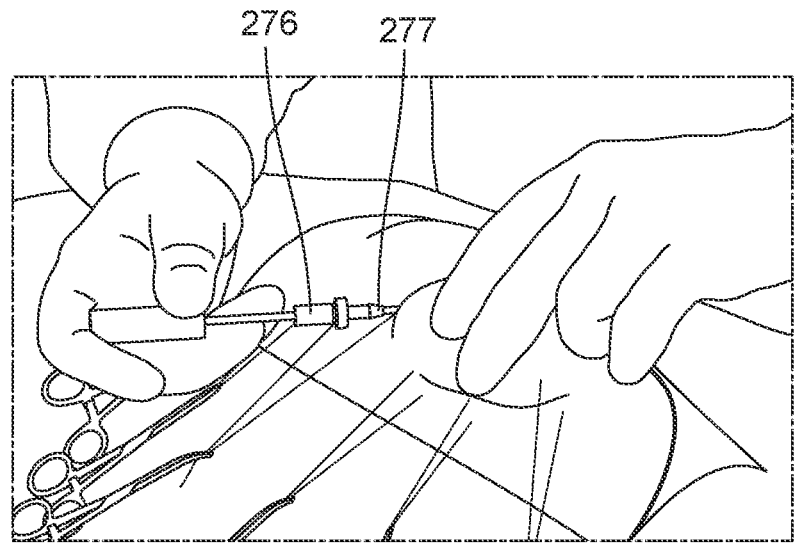
FIG. 34B shows a second step of a method of inserting an infusion cannula into the capsule of a knee, in accordance with one embodiment of the present patent application.

Referring to FIGS. 34A and 34B, in one embodiment, the circular knife 280 is preferably pressed into the tissue of the knee capsule C to form a circular opening in the capsule. The barb 277 at the distal end of the stem of the infusion cannula 276 is desirably advanced into the circular opening formed in the knee capsule. The barb preferably engages an interior wall of the capsule for holding the infusion cannula in place.

Figure 34C:
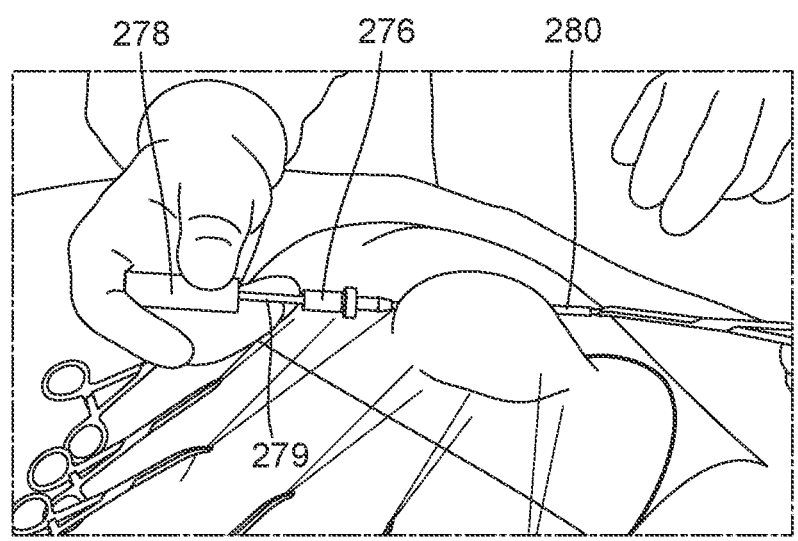
FIG. 34C shows a third step of a method of inserting an infusion cannula into the capsule of a knee, in accordance with one embodiment of the present patent application.
Figure 34D:
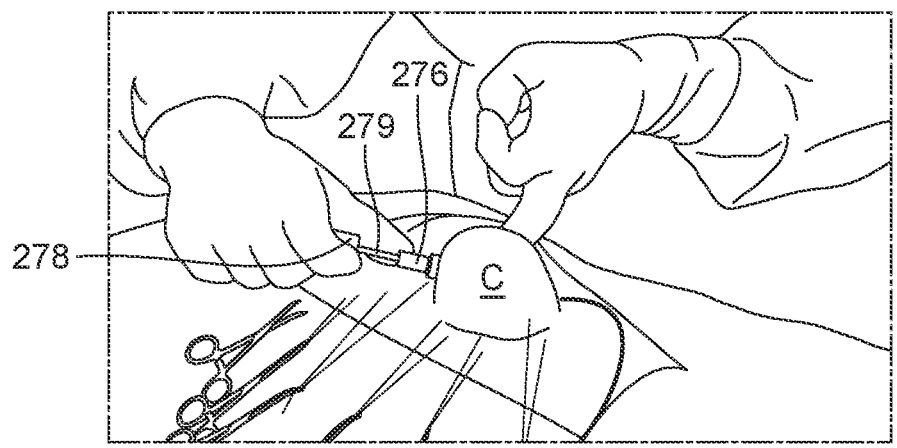
FIG. 34D shows a fourth step of a method of inserting an infusion cannula into the capsule of a knee, in accordance with one embodiment of the present patent application.

Referring to FIGS. 34C and 34D, after the barb at the distal end of the stem of the infusion cannula 276 is positioned within the circular opening formed by the circular knife 280, the circular knife (visible through the surgical opening) is preferably detached from the free end of the insertion tool shaft 279 of the insertion tool 278.

Figure 34E:
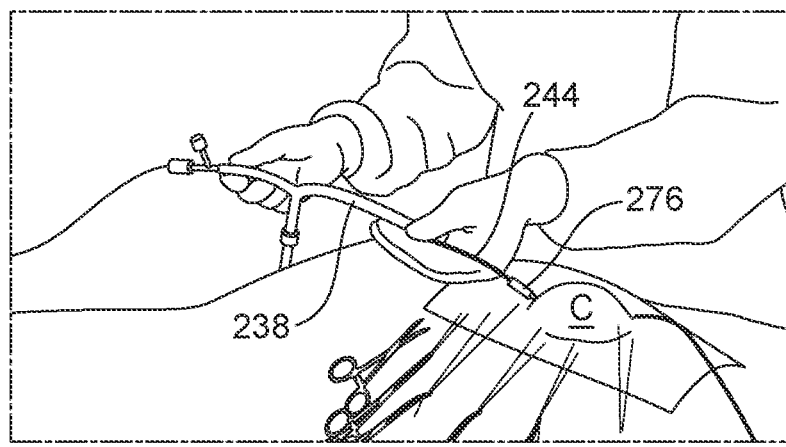
FIG. 34E shows a fifth step of a method of inserting an infusion cannula into the capsule of a knee, in accordance with one embodiment of the present patent application.

Referring to FIGS. 34D and 34E, the insertion tool shaft 279 of the insertion tool 278 is preferably withdrawn from the infusion cannula 276 that is positioned in the capsule C. In one embodiment, the infusion cannula 276 may be coupled with an infusion fluid tube 238 of the fluid supply subsystem for infusing fluid inside the capsule C of a knee. In one embodiment, a pressure transducer 244 is preferably passed through the infusion fluid tube 238 and a central conduit of the infusion cannula 276 for monitoring the pressure of the fluid within the capsule C of the knee.

While the foregoing is directed to embodiments of the present invention, other and further embodiments of the invention may be devised without departing from the basic scope thereof, which is only limited by the scope of the claims that follow. For example, the present invention contemplates that any of the features shown in any of the embodiments described herein, or incorporated by reference herein, may be incorporated with any of the features shown in any of the other embodiments described herein, or incorporated by reference herein, and still fall within the scope of the present invention.

What is claimed is:

1. A system for testing sutures comprising:
   a test bench;
   a framework supporting said test bench above a surface;
   a continuous passive motion (CPM) machine mounted on said test bench, wherein said CPM machine is configured to rotate between a first position in which said CPM machine is upright and located above said test bench and a second position in which said CPM machine is inverted and located below said test bench;
   a fluid supply subsystem for directing a fluid toward said CPM machine;
   a fluid collection tray located below said test bench.

2. The system as claimed in claim 1, further comprising:
   a support rod secured to and extending across an upper end of said framework;
   said test bench comprising a table rotatably mounted to said support rod;
   said CPM machine being secured to said table, wherein said table and said CPM machine are configured to move together between the first position in which said CPM machine is upright and the second position in which said CPM machine is inverted.

3. The system as claimed in claim 2, wherein said framework comprises spaced legs that extend vertically away from the surface, and wherein said table lies in a plane that is parallel to the surface and perpendicular to longitudinal axes of said respective spaced legs.

4. The system as claimed in claim 1, wherein said fluid supply subsystem comprises:
   a fluid feed container;
   a fluid tube having a first end connected with said fluid feed container and a second end spaced from the first end;
   an infusion cannula coupled with the second end of said fluid tube;
   an elevating mechanism coupled with said fluid feed container for selectively raising and lowering said fluid feed container relative to a height of said test bench.

5. The system as claimed in claim 4, wherein said fluid supply subsystem further comprises:
   a pump for circulating the fluid in said fluid supply subsystem;
   a heat exchanger for heating the fluid in said fluid supply subsystem.

6. The system as claimed in claim 5, further comprising a pressure monitoring subsystem coupled with said fluid supply subsystem for monitoring a pressure level of the fluid.

7. The system as claimed in claim 6, wherein said pressure monitoring subsystem comprises:
   a pressure monitoring catheter having a proximal end and a distal end;
   a pressure sensor disposed at the distal end of said pressure monitoring catheter, wherein the distal end of said pressure monitoring catheter passes through said infusion cannula.

8. The system as claimed in claim 7, wherein said CPM machine comprises:
   an upper leg support having an upper leg clamp;
   a lower leg support having a lower leg clamp;
   an articulating joint interconnecting said upper and lower leg supports for enabling said upper and lower leg supports to pivot relative to one another for extending and flexing said CPM machine.

9. The system as claimed in claim 8, wherein:
said CPM machine is capable of securing a cadaver leg, wherein said cadaver leg has a knee with a capsule that is alignable with said articulating joint of said CPM machine;
said infusion cannula is capable of passing through said capsule of said knee for establishing fluid communication between said fluid tube and an intracapsular cavity of said knee for infusing the fluid into the intracapsular cavity.

10. The system as claimed in claim 9, wherein said upper leg clamp is capable of securing an upper part of said cadaver leg to said upper leg support of said CPM machine and said lower leg clamp is capable of securing a lower part of said cadaver leg to said lower leg support of said CPM machine.

11. The system as claimed in claim 10, wherein said infusion cannula is further capable of passing through said capsule of said knee when said knee has a surgical opening formed therein that is closed by one or more sutures.

12. The system as claimed in claim 9, further comprising a system controller in communication with said pressure sensor for monitoring a pressure level of the fluid infused into the intracapsular cavity of said knee.

13. The system as claimed in claim 12, wherein said elevating mechanism comprises:
a winch having a winch cable wound about a spool, said winch cable having a free end that is coupled with said fluid feed container;
a winch handle coupled with said spool for selectively rotating said spool, wherein said winch handle is moveable in a first direction for raising said fluid feed container and is moveable in a second direction for lowering said fluid feed container.

14. The system as claimed in claim 13, wherein the pressure level of the fluid infused into the intracapsular cavity is increased by raising said fluid feed container and the pressure level of the fluid infused into the intracapsular cavity if reduced by lowering said fluid feed container.

15. A system for testing sutures comprising:
a test bench including a rotatable table;
a framework supporting said test bench and said rotatable table above a surface;
a continuous passive motion (CPM) machine mounted on said rotatable table, wherein said CPM machine is configured to rotate between a first position in which said CPM machine is upright and located above said rotatable table and a second position in which said CPM machine is inverted and located below said rotatable table;
a fluid supply subsystem for directing an infusion fluid toward said CPM machine;
a pump for circulating the infusion fluid in said fluid supply subsystem;
a heat exchanger for heating the infusion fluid;
a fluid collection tray located below said CPM machine and said rotatable table;
a pressure monitoring subsystem for monitoring a pressure level of the infusion fluid.

16. The system as claimed in claim 15, further comprising:
said CPM machine including an upper leg support, a lower leg support, and an articulating joint interconnecting said upper and lower leg supports for enabling said upper and lower leg supports to pivot relative to one another for extending and flexing said CPM machine;
said CPM machine including a motor for moving said upper and lower leg supports between the extended and flexed configurations;
wherein said CPM machine is capable of having a cadaver leg positioned on said CPM machine, wherein said cadaver leg has a knee with a capsule that is alignable with said articulating joint of said CPM machine;
said fluid supply subsystem including a fluid feed container, an infusion fluid tube having a first end connected with said fluid feed container and a second end spaced from the first end, and an infusion cannula coupled with the second end of said infusion fluid tube, wherein said infusion cannula is capable of passing through said capsule of said knee for establishing fluid communication between said infusion fluid tube and an intracapsular cavity of said knee.

17. The system as claimed in claim 16, wherein said pressure monitoring subsystem comprises:
a pressure monitoring catheter having a proximal end and a distal end;
a pressure sensor disposed at the distal end of said pressure monitoring catheter, wherein the distal end of said pressure monitoring catheter is capable of passing through said infusion cannula and into the intracapsular cavity of said knee for monitoring the pressure level of the infusion fluid disposed within the intracapsular cavity.

18. The system as claimed in claim 17, wherein said fluid supply subsystem further comprises an elevating mechanism coupled with said fluid feed container for selectively raising and lowering said fluid feed container relative to a height of said test bench, and wherein a pressure level of the infusion fluid is increased by raising said fluid feed container relative to the height of said bench and the pressure level of the infusion fluid is reduced by lowering said fluid feed container relative to the height of said bench.

19. A method of testing performance of sutures comprising:
providing a test bench having a rotatable table configured to rotate between an upright configuration and an inverted configuration;
securing a continuous passive motion (CPM) machine to said rotatable table, said CPM machine including an upper leg support, a lower leg support, and an articulating joint interconnecting said upper and lower leg supports for enabling said upper and lower leg supports to pivot relative to one another for extending and flexing said CPM machine;
with said rotatable table and said CPM machine in the upright configuration, positioning a cadaver leg having a surgical opening closed by one or more sutures on said CPM machine with an upper part of said cadaver leg secured to said upper leg support, a lower part of said cadaver leg secured to said lower leg support, and a knee of said cadaver leg aligned with said articulating joint of said CPM machine;
infusing fluid into an intracapsular cavity of said knee of said cadaver leg;
after the infusing fluid step, activating a motor of said CPM machine for continuously flexing and extending said cadaver leg through a range of motion;
rotating said rotatable table and said CPM machine into the inverted configuration so that said cadaver leg is inverted and located below said rotatable table;
after the rotating step, collecting any of the infused fluid that passes through the surgical opening closed by the one or more sutures.

20. The method as claimed in claim 19, further comprising:
   increasing a pressure level of the fluid infused into the intracapsular cavity of said cadaver leg;
   monitoring the pressure level of the fluid infused into the intracapsular cavity of said cadaver leg.

\* \* \* \* \*